(12) United States Patent
Summerton

(10) Patent No.: US 7,084,248 B2
(45) Date of Patent: Aug. 1, 2006

(54) PEPTIDE COMPOSITION AND METHOD FOR DELIVERING SUBSTANCES INTO THE CYTOSOL OF CELLS

(75) Inventor: James Edward Summerton, Corvallis, OR (US)

(73) Assignee: Gene Tools, LLC, Philomath, OR (US)

( * ) Notice: Subject to any disclaimer, the term of this patent is extended or adjusted under 35 U.S.C. 154(b) by 0 days.

(21) Appl. No.: 10/945,153

(22) Filed: Sep. 20, 2004

(65) Prior Publication Data

US 2006/0014667 A1    Jan. 19, 2006

Related U.S. Application Data

(63) Continuation-in-part of application No. 10/890,886, filed on Jul. 14, 2004.

(51) Int. Cl.
*A61K 38/06* (2006.01)
*A61K 38/00* (2006.01)
(52) U.S. Cl. .......................... 530/326; 514/13
(58) Field of Classification Search ............. 514/2
See application file for complete search history.

(56) References Cited

FOREIGN PATENT DOCUMENTS

WO    WO 96/28468    *    9/1996

OTHER PUBLICATIONS

Tung et al "Arginine Containing Peptide as Delivery Vectors,"Advanced Drug Delivery Reviews 55 (2003), pp. 281-294.*
Moulton et al, "HIV Tat Peptide Enhances Cellular Delivery of Antisense Morpholino Oligomers," Antisense and Nucleic Acid Drug Development (2003) vol. 13 pp. 31-43.*
Kichler et al "Histidine-Rich Amphipathic Peptide antibiotics promote efficient delivery of DNA into Mammalian Cells," PNAS (2003), vol. 100 pp. 1564-1568.*
Niidome et al, "Chain Length of Cationic alpha-helical Peptide Sufficient for Gene Delivery into Cells," Bioconjugate Chem., 1999, vol. 10, 773-780.*
Gavel et al, "Mitochondria targeting sequences : Why 'non-amphiphilic peptide may still be amphiphilic," Feb. (1988) vol. 235, 173-177.*
Fisher et al "Cellular Delivery of Impermeable Effector Molecules in the Form of Conjugates with Peptides Capable of Mediating Membrane Translocation," Bioconjugate Chemistry (2001) vol. 12, pp. 825-841.*
Moulton H.M., Peptide-assisted delivery of steric-blocked antisense oligomers, Current Opinion in Molecular Therapeutics, (2003) 5(2):123-132.*
Ho et al, "Synthetic Protein Transduction Domains : Enhanced Transduction Potential in Vitro and in Vivo," Cancer Research (2001), vol. 61, pp. 474-477.*
Creighton, Proteins and Molecular Properties (2nd Edition), pp. 184-186.*
Midoux, P. et al: Bioconjugate Chemistry 9: 260, 1998). pp. 260-267.

* cited by examiner

*Primary Examiner*—Bruce R. Campell
*Assistant Examiner*—Thomas S. Heard
(74) *Attorney, Agent, or Firm*—Lori M. Friedman

(57) ABSTRACT

Weak-base amphiphilic delivery peptide compositions are described for use in delivering large polar substances (cargo) into the cytosol of animal cells via an indirect endocytosis-mediated delivery process. The delivery peptides, which are predominantly non-ionic at neutral pH, bind but do not permeabilize cell membranes. After endocytosis of both delivery peptides and cargo, acidification of the endosome converts the delivery peptides to their polycationic form, whereupon they permeabilize the endosomal membrane and allow co-endocytosed cargo to pass from the endosome to the cytosol of the cell.

26 Claims, 17 Drawing Sheets

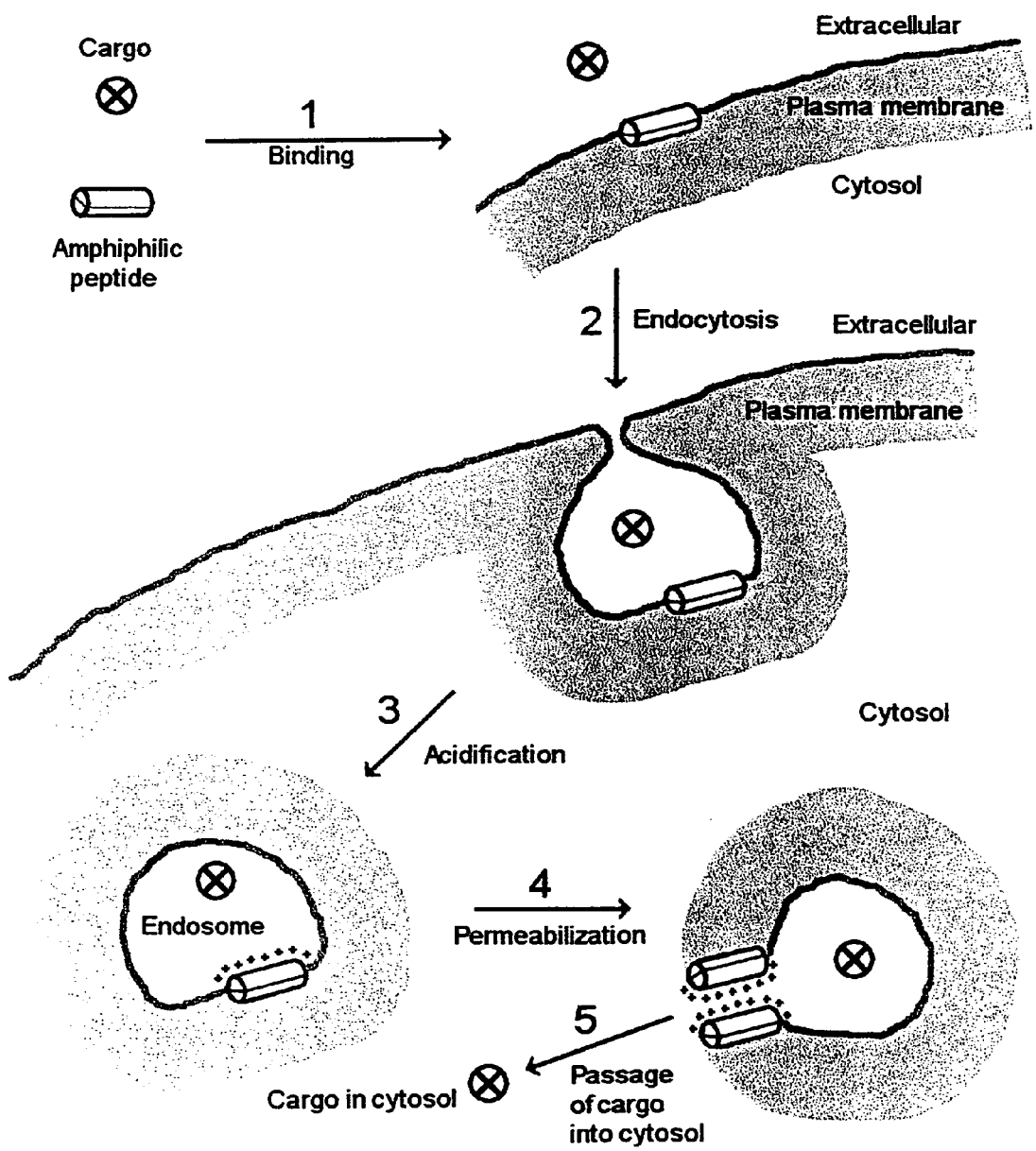
Figure 1. Probable steps in cytosolic delivery of cargo by weak-base amphiphilic peptides Figure 2: Cytosolic delivery by short weak-base amphiphilic delivery peptides in absence and presence of serum.
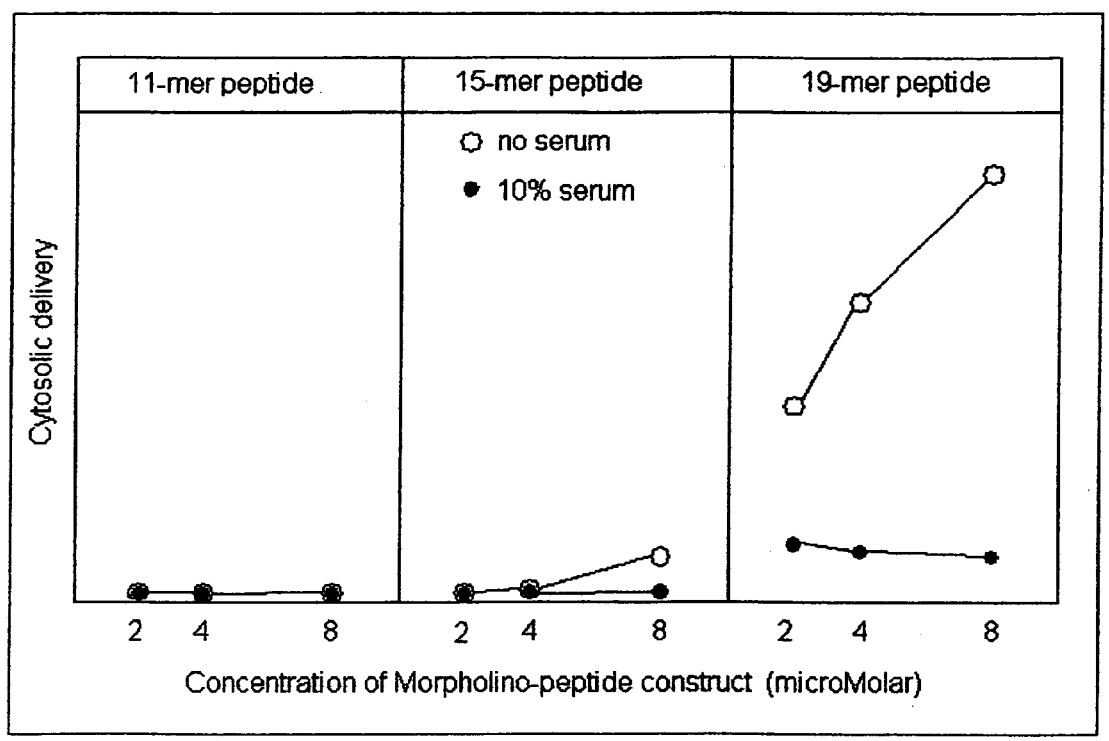

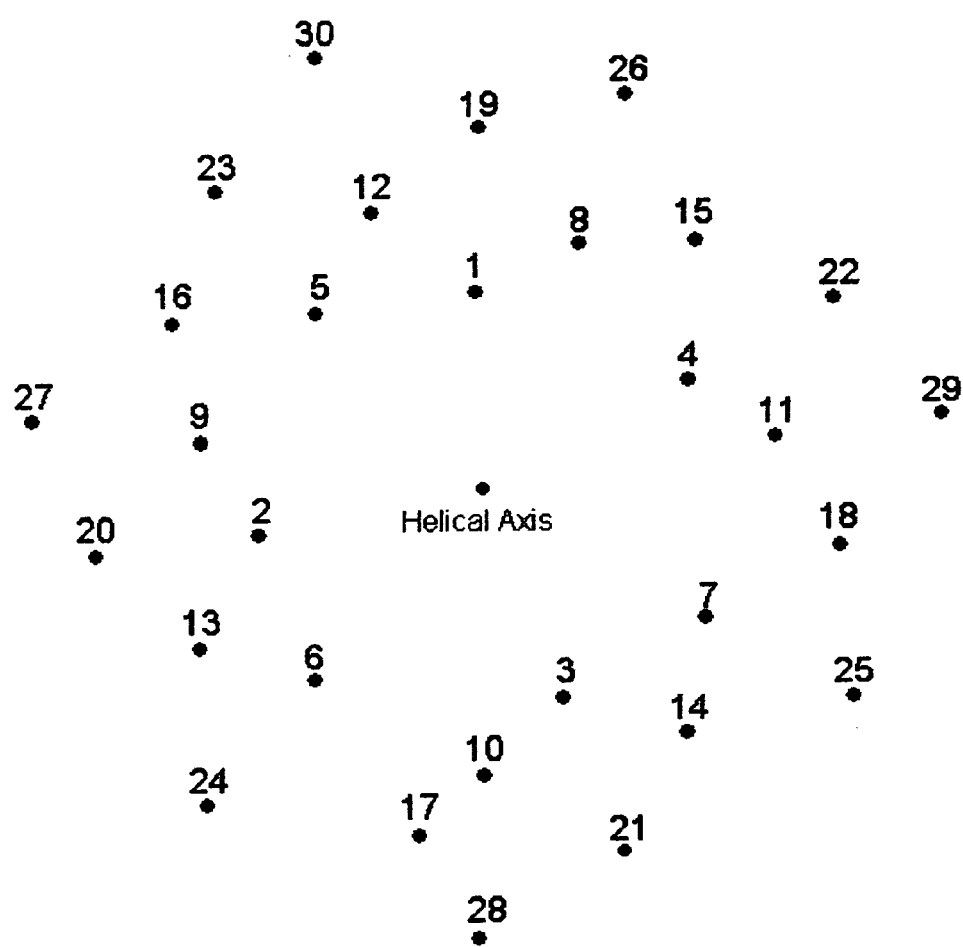
Figure 3. Axial distribution plot of amino acid side chains in a 30-mer alpha helical peptide.

Figure 4. Axial distribution and linear presentation of amino acid side chains for an amphiphilic peptide having a 160 degree weak-base face.
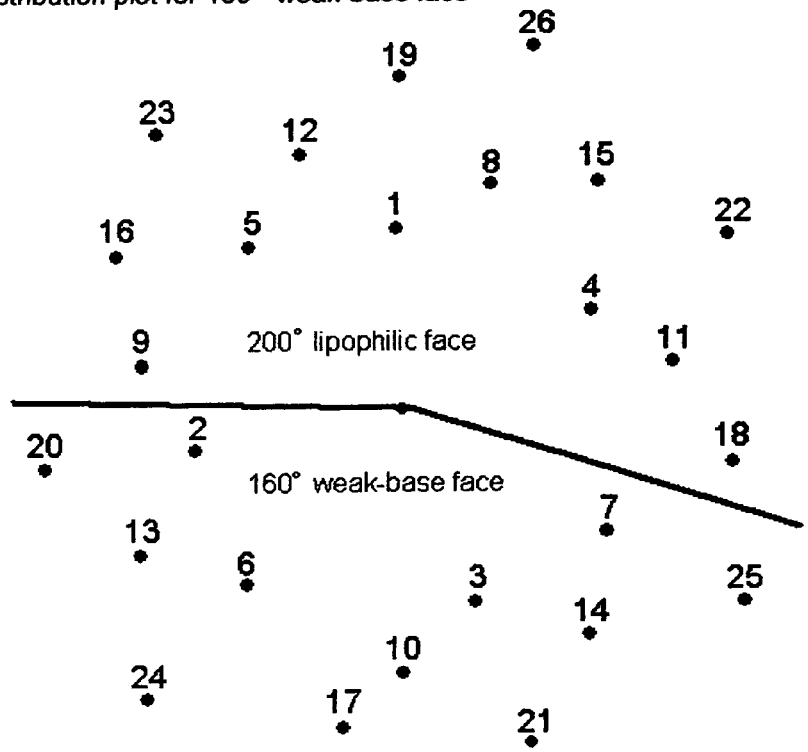

Figure 5. Axial distribution and linear presentation of amino acid side chains for an amphiphilic peptide having a 200 degree weak-base face.
a. Axial distribution plot for 200° weak-base face
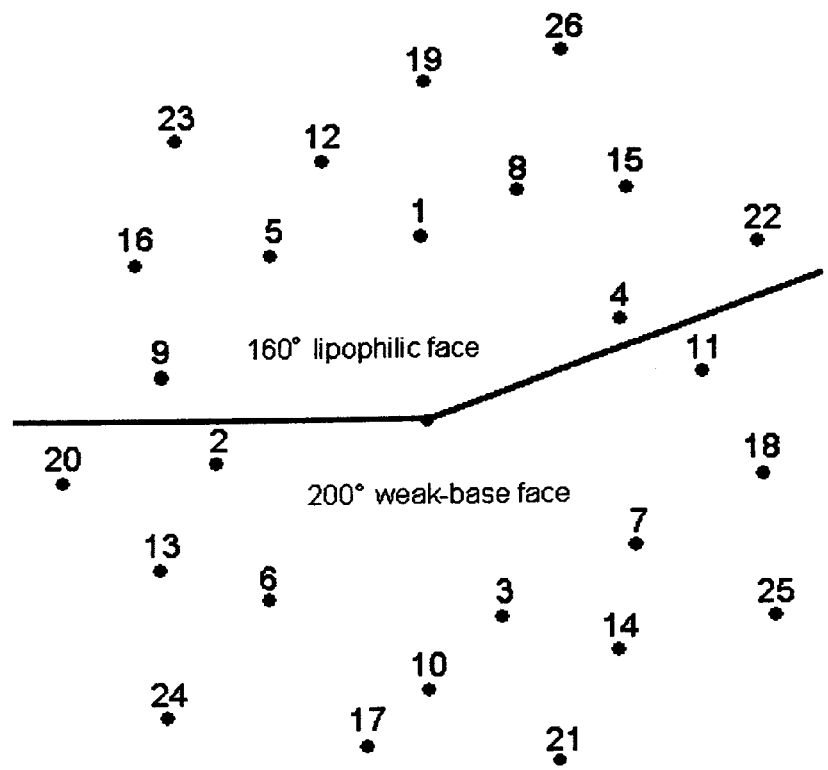
b. Linear presentation
```
                1 2 3 4 5 6 7 8 9 10 11 12 13 14 15 16 17 18 19 20 21 22 23 24 25 26
Lipophilic face: L  L L   L L       L        L  L        L       L L        L
Weak-base face:  HH   H H    H H      H H       H H  H H        H H
```

Figure 6. Cytosolic delivery by peptides with varying face sizes.
a. No serum, cargo not linked to delivery peptide
(cargo 1 microMolar; delivery peptide: 13 microMolar)
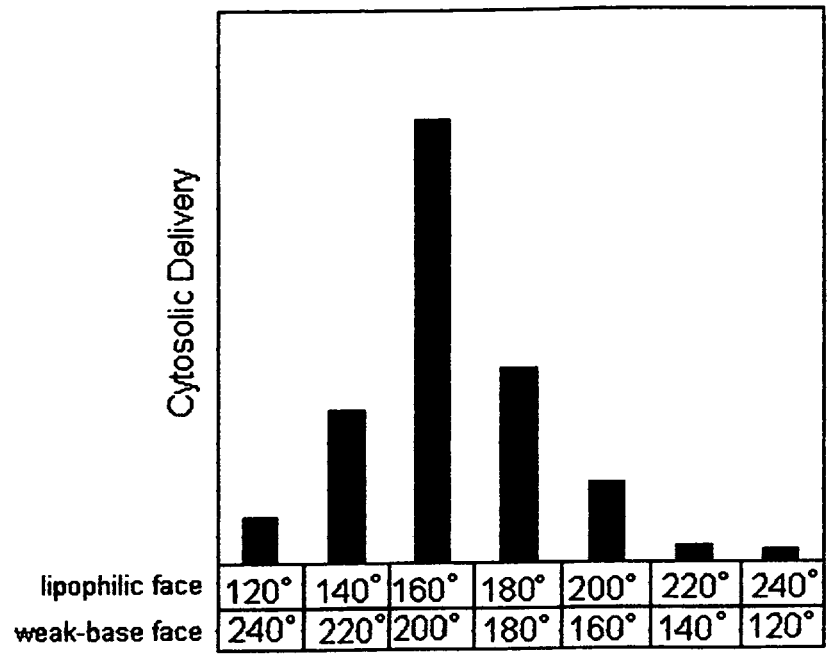
b. 5% serum, cargo not linked to delivery peptide
(cargo: 1 microMolar; delivery peptide 13 microMolar)
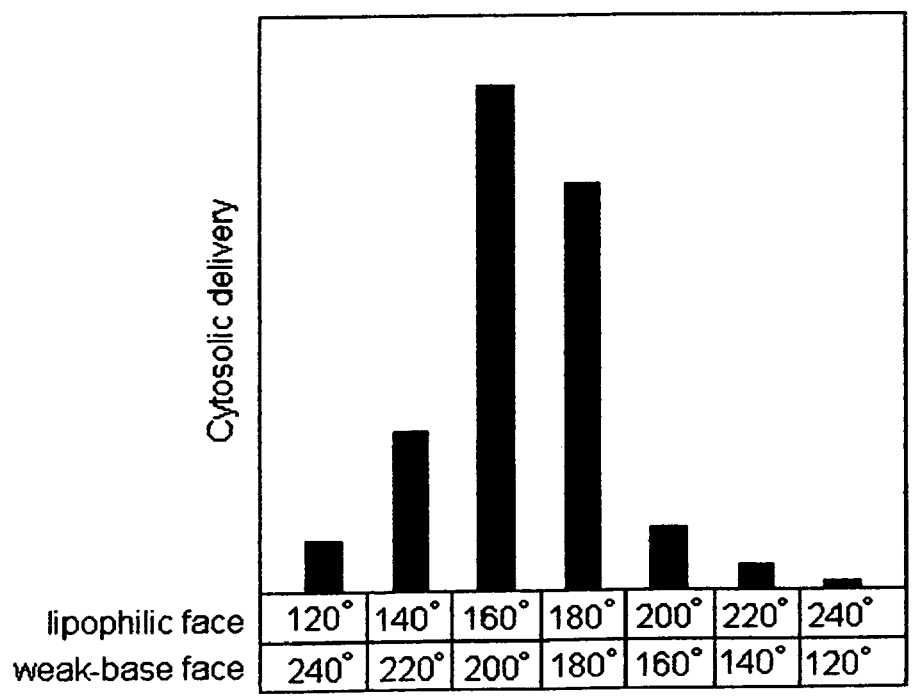

Figure 7. Aqueous solubility of delivery peptides with varying numbers of histidines replaced by lysines.
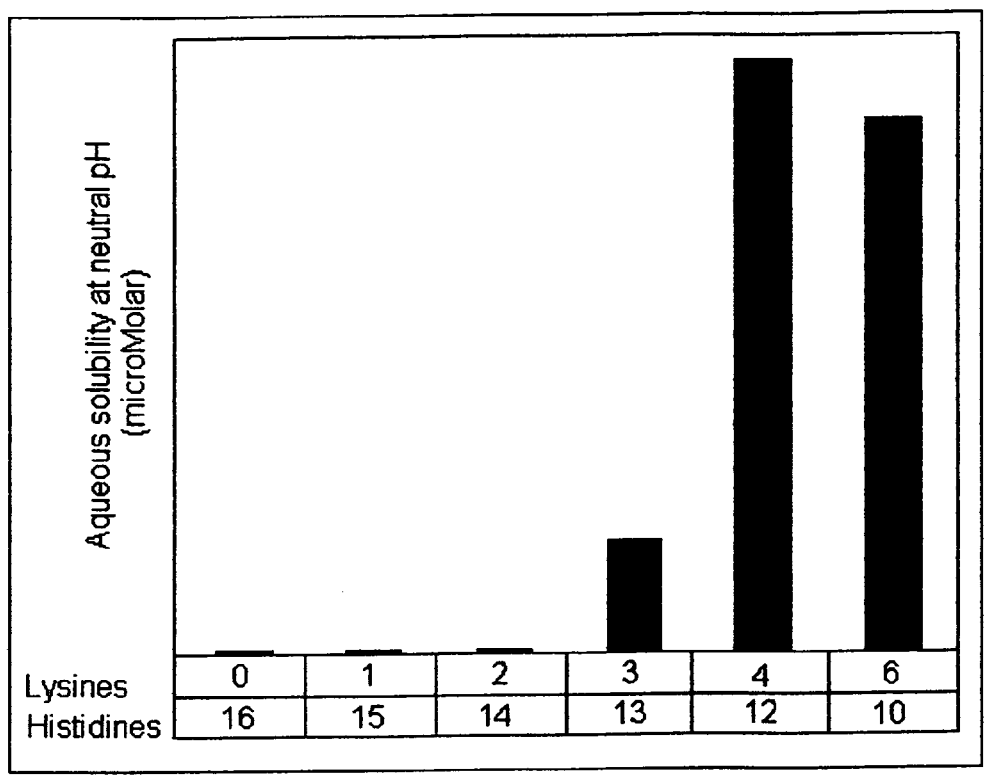

Figure 8. Cytosolic delivery compared for a peptide with an all-histidine weak-base face versus a peptide with a 3-lysine/13-histidine weak-base face.
a. Delivery of cargo not linked to delivery peptide (cargo: 5 microMolar)
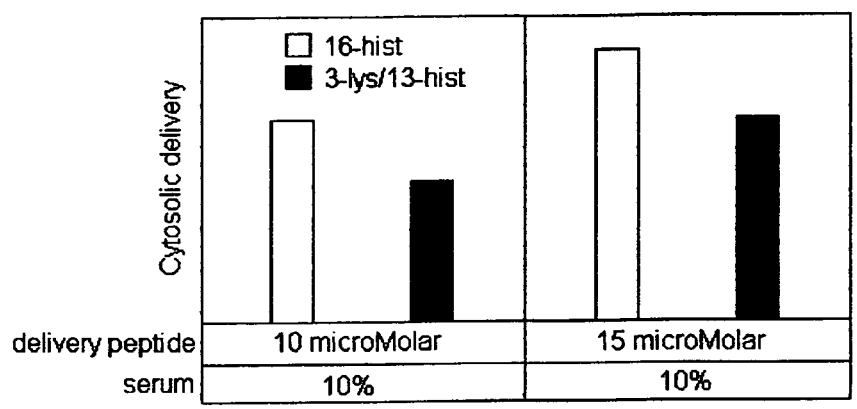
b. Delivery of cargo linked to delivery peptide, plus added delivery peptide (cargo-delivery peptide: 1 microMolar)
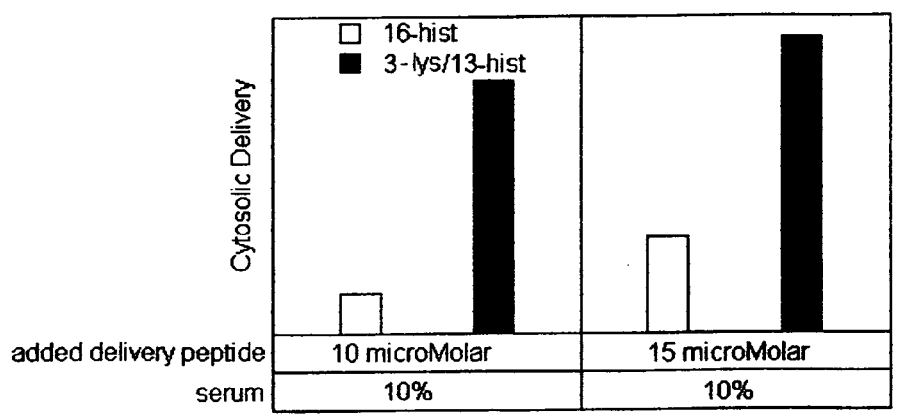

Figure 9. Unacceptable, acceptable, and preferred distributions of strong-base amino acids along the length of weak-base amphiphilic delivery peptides.

a. Unacceptable distribution of lysines (K)

```
                 1 2 3 4 5 6 7 8 9 10 11 12 13 14 15 16 17 18 19 20 21 22 23 24 25 26
Lipophilic face: L   L L   L L         L        L  L        L        L  L        L
Weak-base face:   H H   H H     H K      H K         K H      H H        H H
``` b. Acceptable distribution of lysines (K)

```
                 1 2 3 4 5 6 7 8 9 10 11 12 13 14 15 16 17 18 19 20 21 22 23 24 25 26
Lipophilic face: L   L L   L L         L        L  L        L        L  L        L
Weak-base face:   H K   H H     H K      H H         H K      H H        H H
``` c. Preferred distribution of lysines (K)

```
                 1 2 3 4 5 6 7 8 9 10 11 12 13 14 15 16 17 18 19 20 21 22 23 24 25 26
Lipophilic face: L   L L   L L         L        L  L        L        L  L        L
Weak-base face:   H K   H H     H H      H K         H H      H H        H K
```

Figure 10. Cytosolic delivery as a function of the length of the delivery peptide.
a. Delivery of cargo linked to delivery peptide
   (cargo-peptide construct: 8 microMolar)
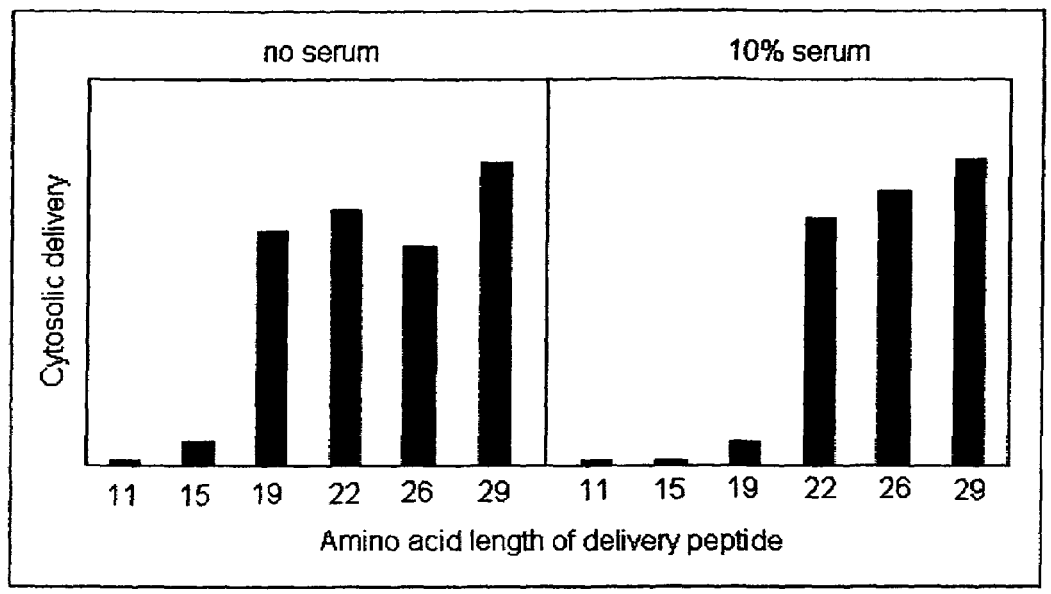
b. Delivery of cargo not linked to delivery peptide
   (cargo: 1 microMolar; delivery peptide: 13 microMolar)
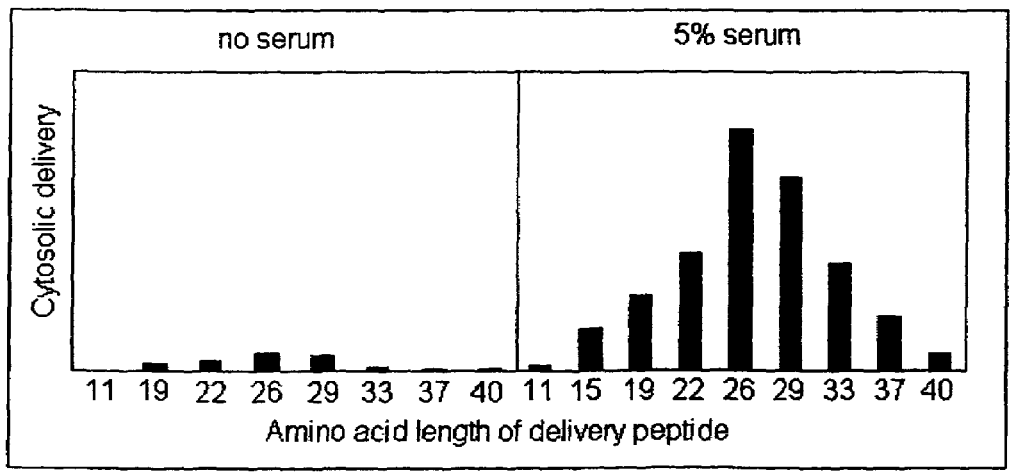

Figure 11. Cytosolic delivery by identical-sequence peptides differing in their C-terminal structures.
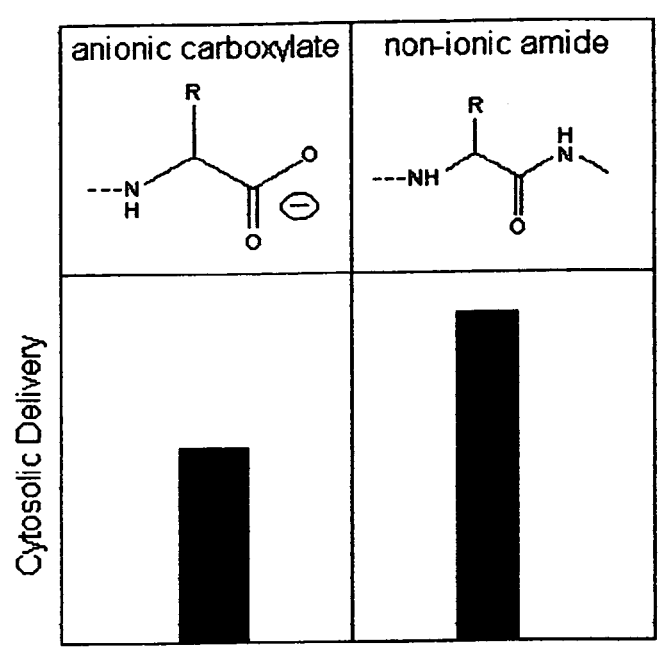

Figure 12. Cytosolic delivery by identical-sequence peptides differing in their N-terminal structures.
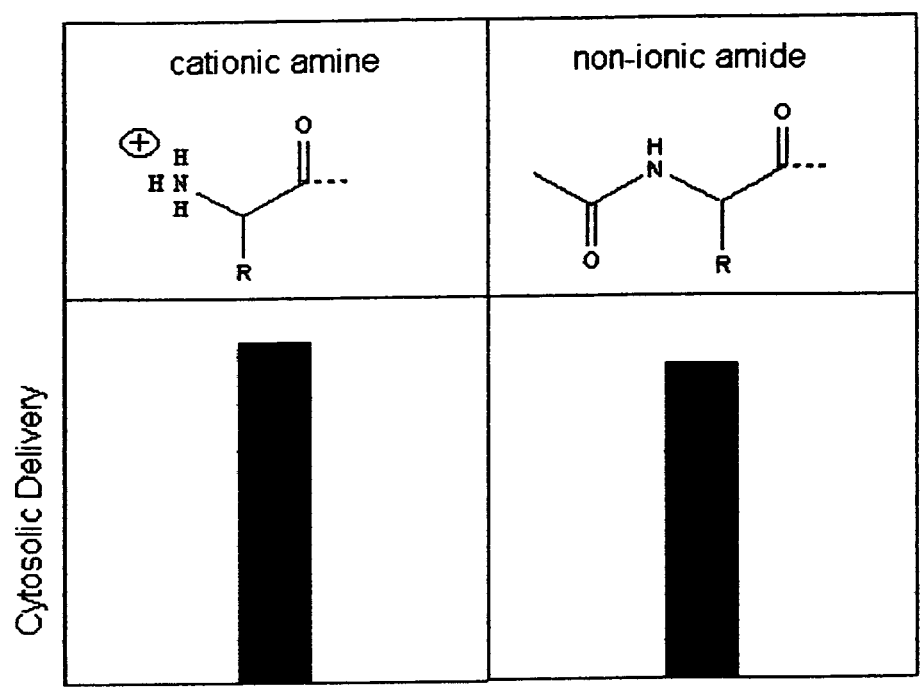

Figure 13a) PRIOR ART
Comparison of semi-natural weak base peptide of Midoux (1998)
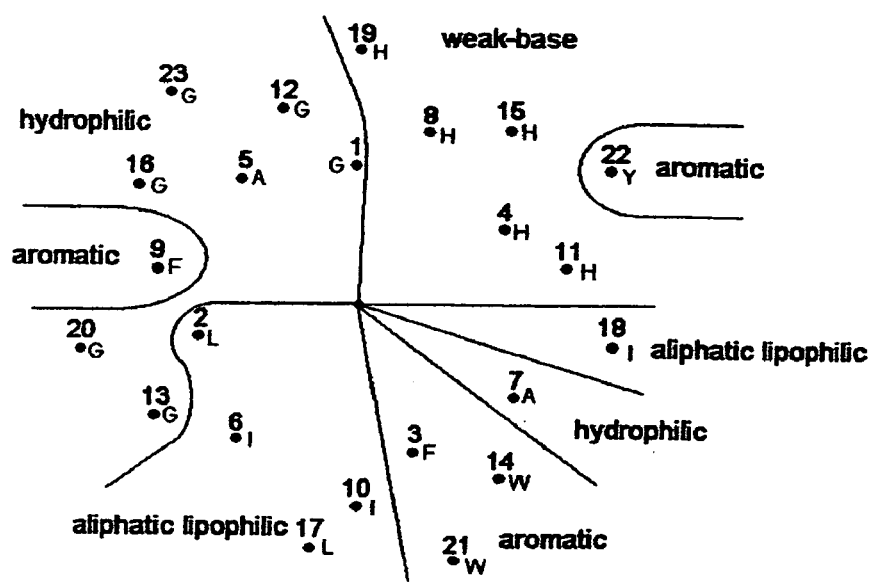

Representative designed delivery peptide of instant invention

Figure 14. Coupling a delivery peptide to a representative cargo.
a)
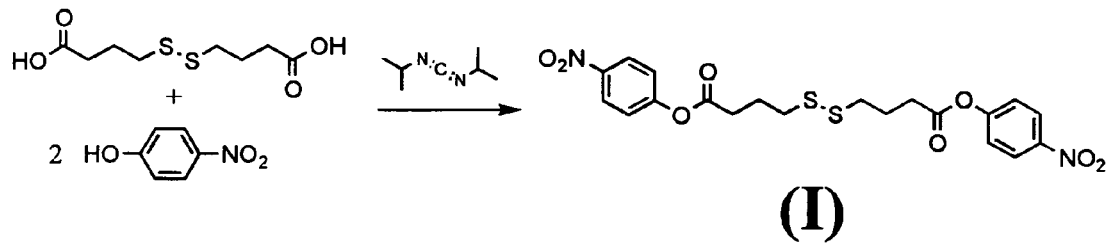
b)
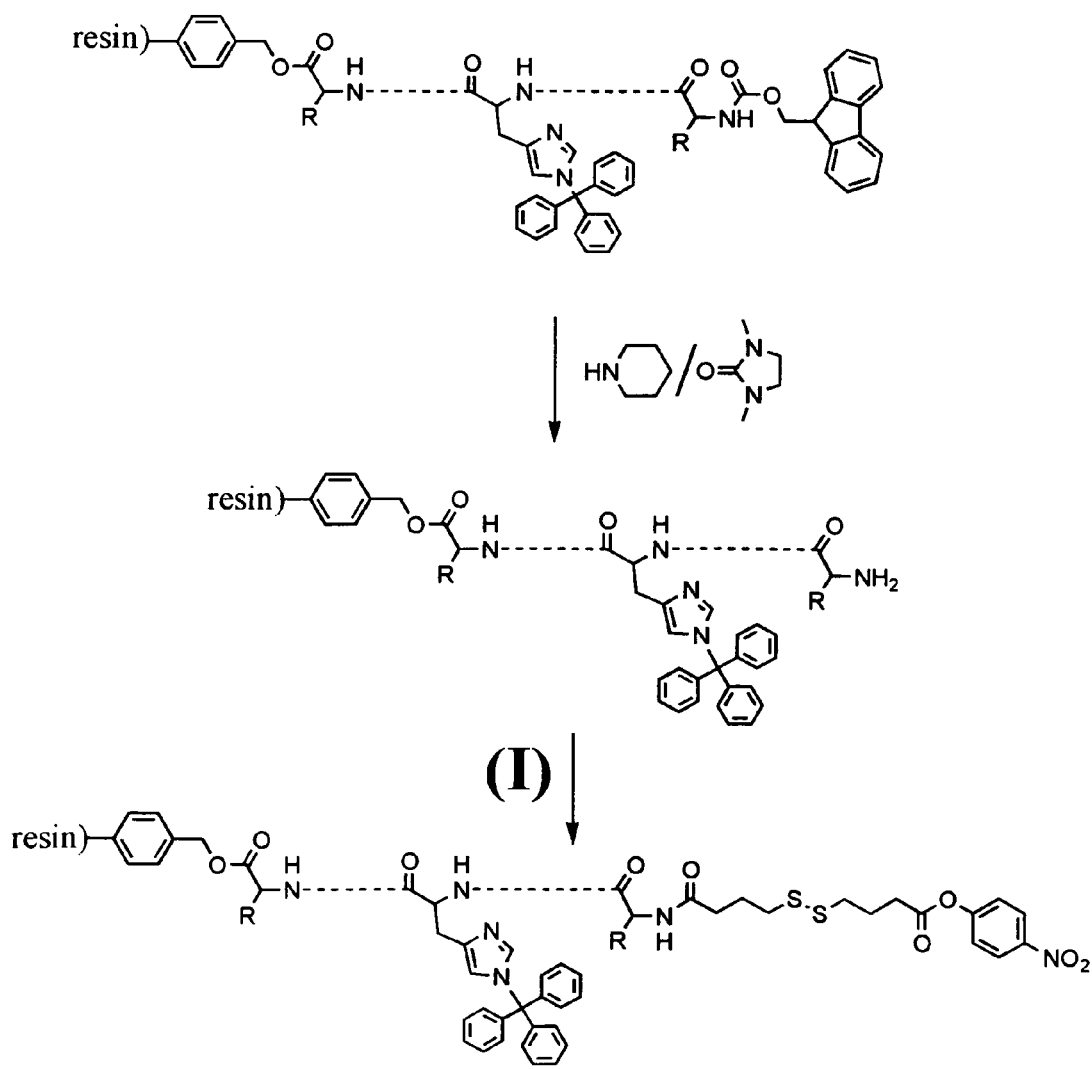

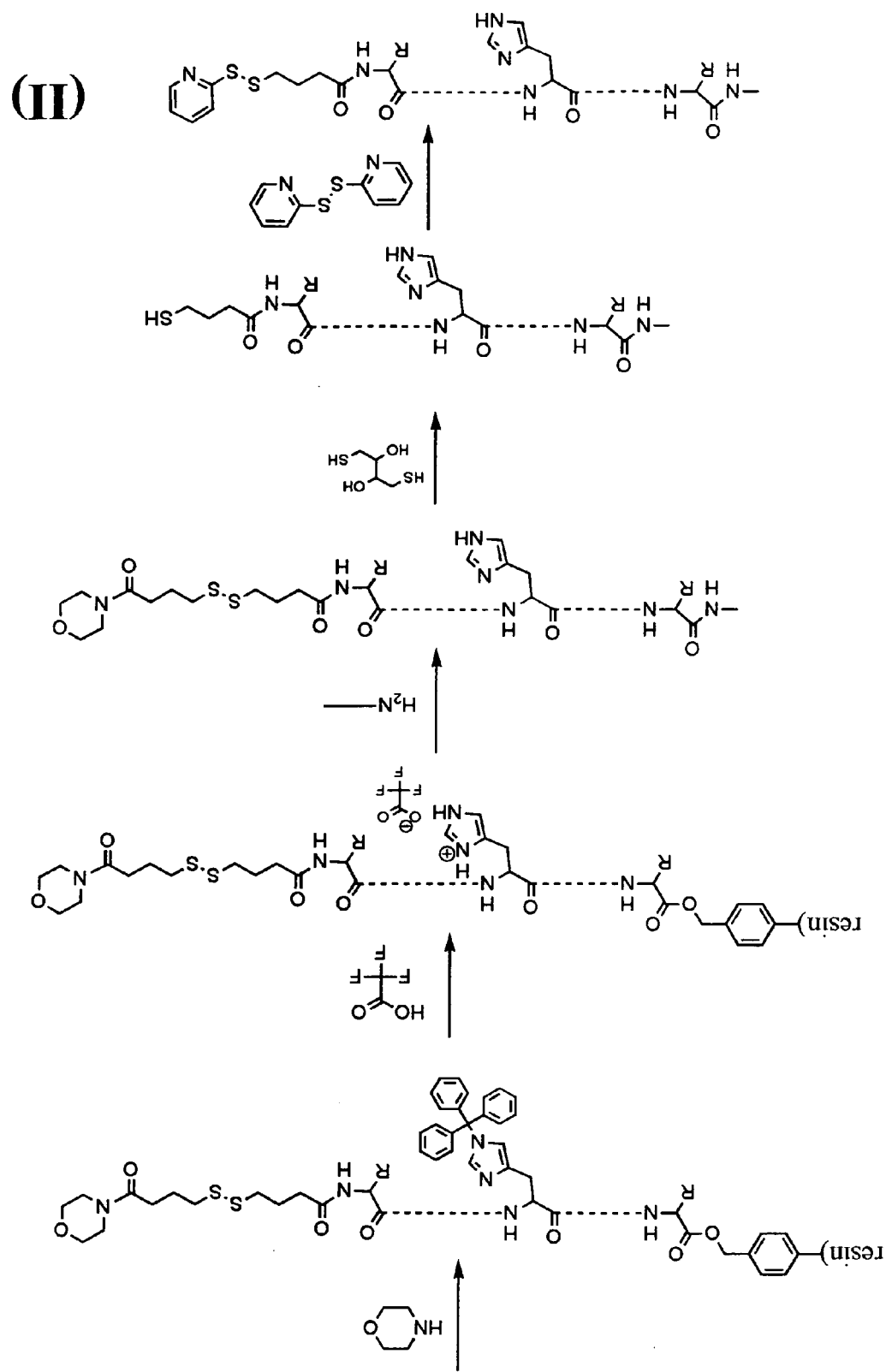

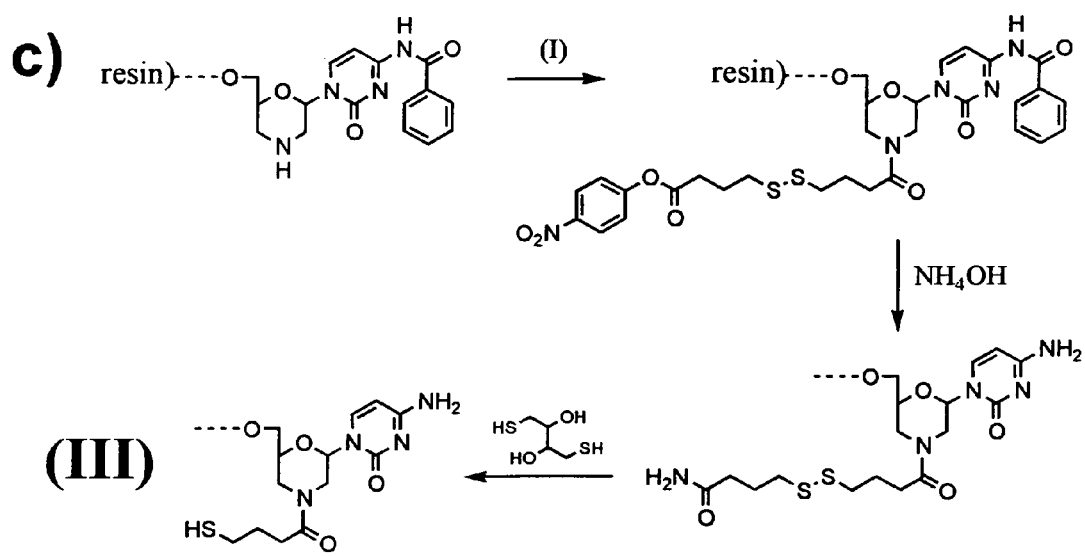
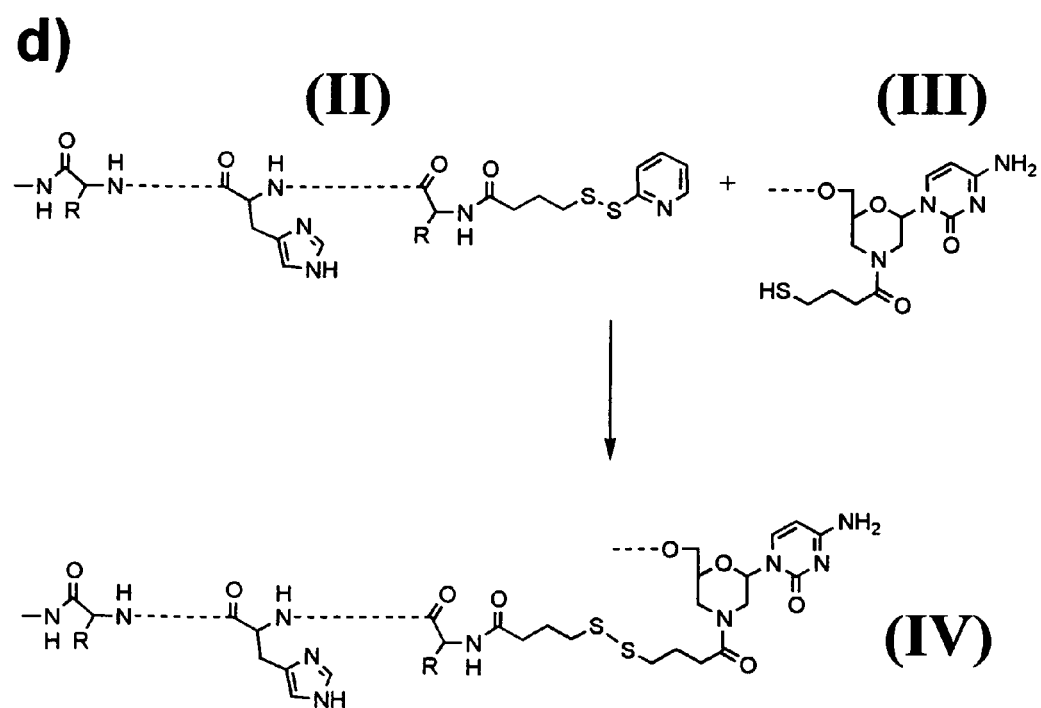

PEPTIDE COMPOSITION AND METHOD FOR DELIVERING SUBSTANCES INTO THE CYTOSOL OF CELLS

RELATED PATENT APPLICATIONS

This application is a continuation-in-part of U.S. patent application Ser. No. 10/890,886 filed on Jul. 14, 2004, which is herein incorporated by reference.

1. FIELD OF THE INVENTION

The invention relates to the use of weak-base amphiphilic peptide compositions effective for delivering substances into the cytosol of animal cells. The compositions are predominantly non-ionic at neutral pH, but become polycationic at the acidic pH within endosomes.

2. BACKGROUND OF THE INVENTION

Over the past several decades methods have been devised for constructing genetic elements effective to code for virtually any desired gene product; and for preparing antisense oligos and related substances effective for modifying the expression of virtually any gene; and for preparing peptides and proteins effective for directly acting within cells. A major limitation in utilizing such new technologies for a host of valuable research and therapeutic applications has been the difficulty of efficiently delivering large polar substances into the cytosol of animal cells without incurring undue damage to those cells. Thus, a simple, safe, and effective means for delivering large polar substances into animal cells has many immediate and valuable applications in biological and medical research, and may also have a wide range of therapeutic applications in the near future.

While a number of delivery systems are currently available for delivering large polar substances into the cytosol of cells, most of these delivery systems suffer from at least one, and usually several of the following limitations: substantial toxicity to the recipient cells; low efficiency, particularly in the presence of even a few percent of serum; undue complexity of use; and, poor reliability and reproducibility. Such delivery systems include ones developed by the applicant: scrape delivery (Partridge, 1996); weak-acid transport engines (Summerton, 2000); osmotic delivery (Morcos, 2001); and, mixed-base polyamines (Morcos, 2001). In addition, many other types of delivery systems have also been developed, including: microinjection (Chin, 1990); multiple types of liposomes (Thierry, 1992); streptolysin O (Spiller, 1995); electroporation (Bergan, 1996); strong-base polyamines (Boussif, 1995); multiple natural and designed strong-base peptides (Lemaitre, 1987; Derossi, 1994); and, natural and designed weak-acid peptides (Pichon, 1997).

Further, a number of viral and excreted cellular proteins are known to penetrate animal cell membranes, often by virtue of a short strong-base (polycationic at neutral pH) amphiphilic segment of the protein, typically with a segment length of around 12 to 18 amino acids. Such sequences are commonly referred to as "protein transduction domains". Representative well-studied examples include a short segment of tat protein of the HIV virus (Mann, 1991), a short segment of the VP22 protein of Herpes virus (Elliott, 1997), and a short segment of an excreted neural protein of the fruit fly (Derossi, 1994).

Synthetic versions and close analogs of these membrane penetrating peptide sequences have been developed and used to deliver a variety of substances into animal cells. Such membrane penetrating peptides typically contain a lipophilic face or end, plus a face or end containing multiple strong-base amino acids selected from arginine and lysine. This peptide structural type consisting of both a lipophilic region and a strong-base region has been further developed by Prochiantz and coworkers (described in PCT published Patent application WO 97/12912) to give a designed peptide of tryptophans and arginines—affording a peptide with a membrane penetrating capacity substantially greater than natural peptide sequences reported to date. Applicant has designed and developed a different series of strong-base peptides composed of leucines and lysines, and cell testing results indicate that such peptides have a still greater membrane penetrating capacity (unpublished results).

Many of these systems, particularly the natural and designed strong-base peptides, are reasonably effective for delivering large polar substances into the cytosol of cells. However, they are typically of limited utility because of their toxicity to cells. To a large extent this appears to be because their delivery mechanism entails permeabilizing the plasma membrane, which allows loss from the cells of salts, sugars, vitamins, amino acids, nucleotides, and a host of other essential cellular constituents.

It has been postulated that such toxicity could be largely avoided by developing delivery systems which utilize an indirect endocytosis-mediated delivery mechanism wherein the plasma membrane is never permeabilized.

In an effort to reduce the toxic effects commonly incurred with direct-entry delivery systems, several mixed-base delivery systems have been developed with the goal of achieving indirect delivery via endocytosis. One representative mixed-base system uses polylysine wherein the lysine side chains are acylated with histidines (Pichon, 2000). This gives a polymeric composition wherein the strong-base alpha-amino moieties of the histidines serve to bind electrostatically to the negatively charged surface of the plasma membrane of cells. Subsequent endocytosis and acidification within the endosome serves to ionize the weak-base imidazole moieties of the histidines giving a composite charge density on the polymeric composition sufficient to permeabilize the endosomal membrane. This allows co-endocytosed substances (cargo) to pass from the endosome into the cytosol of the cell.

Another mixed-base delivery system is marketed by GENE TOOLS, LLC. It utilizes ethoxylated polyethyleneimine (EPEI) for delivering Morpholino antisense oligos into the cytosol of cultured cells (Morcos, 2001). EPEI contains in roughly equal portions both moderately strong base moieties having pKa values above pH 7, and weaker-base moieties having pKa values in the range of about 5.5 to 7. In this delivery system the higher-pKa base moieties of EPEI (ionized at neutral pH) serve to bind electrostatically to the negatively charged surface of the plasma membrane of cells. Subsequent endocytosis and acidification within the endosome serves to ionize the weaker-base moieties, resulting in a composite charge density on the EPEI sufficient to permeabilize the endosomal membrane, thereby allowing co-endocytosed cargo to pass from the endosome through the permeabilized endosomal membrane into the cytosol of the cell.

While these mixed-base delivery systems are indeed less toxic to cells than the strong-base delivery systems, nonetheless, they are still somewhat toxic. In addition, their efficiency is much reduced in the presence of just a few percent of serum. This poor activity in the presence of serum, a problem shared with most other delivery systems, is a significant limitation because numerous cell types, particularly primaries, are damaged in the absence of serum.

The good efficacy with reduced toxicity seen with mixed-base delivery systems suggested the possibility that simply deleting most or all of the strong-base moieties (cationic at neutral pH) while keeping the weak-base moieties (non-ionic at neutral pH) might alleviate the cell toxicity problem. A paper in the scientific literature indicates that something along this line has already been reported (P. Midoux, et al: Membrane permeabilization and efficient gene transfer by a peptide containing several histidines. Bioconjugate Chemistry 9: 260, 1998). Initially other workers had identified an anionic peptide from the N-terminal segment of the HA-2 subunit of the influenza virus hemaglutinin which is involved in fusion of the viral envelope with the endosomal membrane upon acidification of the endosome (Plank, 1994). That peptide sequence was subsequently modified slightly to increase its acid-triggered membrane permeabilization properties (Murata, 1991). Thereafter, the modified sequence was further modified by replacing its anionic moieties with cationic lysines to give a strong-base version of the originally-polyanionic peptide (Murata, 1992). While this strong-base version was effective for permeabilizing cell membranes, albeit with significant toxicity, that permeabilizing activity was largely lost in the presence of serum.

With the objective of decreasing toxicity and achieving activity in the presence of serum, Midoux and co-workers subsequently replaced the 5 lysines of the peptide with 5 histidines (Midoux, 1998), to give a peptide with four amino acid types (5 weak-base histidines, 8 non-ionic hydrophilic amino acids, 5 aliphatic lipophilic amino acids, and 5 aromatic lipophilic amino acids). Since glycines disfavor the alpha helical conformation, because of this peptide's high and well dispersed glycine content, this peptide most likely exists in a largely unstructured random coil in aqueous solution. FIG. 13a of the instant application shows the sequence of this peptide (prior art).

It is also noteworthy that in this semi-natural peptide developed by Midoux only a minority (44%) of the side chains appear optimal for membrane binding and subsequent pH-triggered permeabilization. More specifically, only 22% (the L and I side chains) appear optimal for membrane binding, and only 22% (the H side chains) are expected to contribute to membrane permeabilization upon acidification within the endosome. It seems likely that the remaining majority of the side chains (56%) of this peptide may have served in the original natural peptide sequence to properly integrate that sequence into the rest of the protein in which it was an integral part.

In sharp contrast to the case for the semi-natural unstructured weak-base peptide of Midoux, the designed peptides of the instant invention, as illustrated in FIG. 13b, have an amino acid composition that virtually assures a regular alpha helical conformation at neutral pH. In that alpha helical conformation the peptide has two precisely delineated faces, a lipophilic face and a weak-base face. Most or all side chains of the lipophilic face serve explicitly for membrane binding at neutral pH, and most or all side chains of the weak-base face contribute to membrane permeabilization upon acidification within the endosome. Thus, in these designed highly structured delivery peptides of the instant invention most or all of the side chains are designed to be both optimal for and suitably positioned to carry out the two key functions required for an indirect endocytosis-mediated cytosolic delivery process, those two functions being: a) membrane binding by the lipophilic face at neutral pH; and, b) membrane permeabilization by the weak-base face at acidic pH.

While the weak-base peptide of Midoux does achieve delivery of cargos into cultured cells, even in the presence of serum, the experience of Prochiantz in designing from scratch a highly effective tryptophan/arginine peptide and my experience in designing from scratch an even more effective leucine/lysine peptide (unpublished results) led me to speculate that it might be possible to substantially improve delivery efficiency, reduce toxicity, and achieve better activity in the presence of serum by creating from scratch a delivery agent expressly designed and optimized for indirect endocytosis-mediated cytosolic delivery.

SUMMARY OF THE INVENTION

The instant invention comprises a novel peptide composition and method for indirectly delivering large polar substances into the cytosol of animal cells. This new indirect endocytosis-mediated delivery system causes little or no toxicity to the recipient cells, is quite effective even in the presence of serum, is simple to use, and generally provides more reliable and reproducible results than prior art delivery systems.

The peptide composition of the invention (the delivery peptide) comprises a two-face amphiphilic peptide, with one face composed predominantly (80% to 100%) of aliphatic lipophilic amino acids, and the other face composed predominantly (80% to 100%) of basic amino acids, with at least 70% of the amino acids of the weak-base face being histidines. At neutral pH, such as in the extracellular medium and within the cytosol of cells, the delivery peptide exists in a state which binds but does not permeabilize membranes, while at acidic pH, such as within endosomes, the delivery peptide reversibly converts to a polycationic state effective to permeabilize cell membranes.

Diverse lines of evidence suggest that delivery of a large polar substance (the cargo) with this new system entails the steps illustrated in FIG. 1. The delivery peptide and the substance to be delivered (cargo) are added to the cells. The cargo may be either free (as shown in FIG. 1) or linked to the delivery peptide (not shown). Initially the lipophilic face of the delivery peptide binds to the outer surface of the cell's plasma membrane (step 1). Thereafter, normal endocytosis by the cell results in co-engulfment of both the membrane-bound delivery peptide and cargo in the medium or bound to the cell surface (step 2). Subsequent natural acidification of the endosome causes ionization of the histidines of the delivery peptide (step 3). This converts the delivery peptide to its polycationic state which acts to permeabilize the endosomal membrane (step 4), allowing the cargo to pass from the endosome through the permeabilized membrane into the cytosol of the cell (step 5). Importantly, any delivery peptide which escapes to the pH-neutral cytosol is immediately converted back to its non-permeabilizing state, thereby precluding toxicity due to permeabilization of other cellular membranes.

BRIEF DESCRIPTION OF THE DRAWINGS

FIG. 1. Probable steps in cytosolic delivery of cargo by weak-base amphiphilic delivery peptides FIG. 2. Cytosolic delivery by short weak-base amphiphilic delivery peptides in absence and presence of serum FIG. 3. Axial distribution plot of amino acid side chains in a 30-mer alpha helical peptide FIG. 4. Axial distribution and linear presentation of amino acid side chains for an amphiphilic peptide having a 160 degree weak-base face FIG. 5. Axial distribution and linear presentation of amino acid side chains for an amphiphilic peptide having a 200 degree weak-base face FIG. 6. Cytosolic delivery by peptides with varying face sizes FIG. 7. Aqueous solubility of delivery peptides with varying numbers of histidines replaced by lysines FIG. 8. Cytosolic delivery compared for a peptide with an all-histidine weak-base face versus a peptide with a 3-lysine/13-histidine weak-base face FIG. 9. Unacceptable, acceptable, and preferred distributions of strong-base amino acids along the length of weak-base amphiphilic delivery peptides FIG. 10. Cytosolic delivery as a function of length of the delivery peptide FIG. 11. Cytosolic delivery by identical-sequence peptides differing in their C-terminal structures FIG. 12. Cytosolic delivery by identical-sequence peptides differing in their N-terminal structures FIG. 13. Comparison of semi-natural weak-base peptide of Midoux (1998), FIG. 13a (Prior Art) and representative weak-base amphiphilic peptide of the instant invention FIG. 13b.

FIG. 14. Three page figure of coupling a delivery peptide to a representative cargo

DEFINITIONS USED IN THIS INVENTION

Figure 13B:
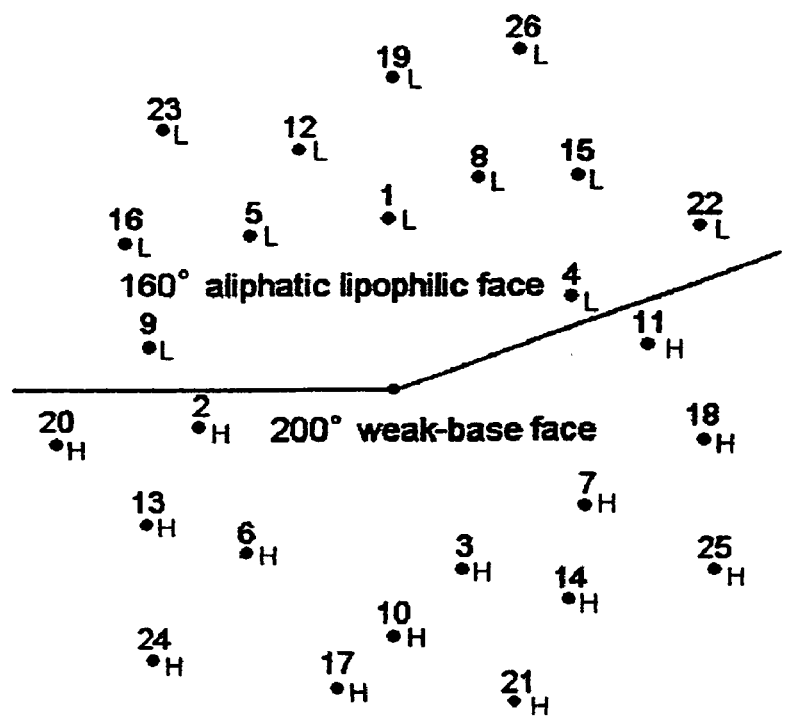

The terms used herein have the following specific meanings, unless otherwise noted.

"Large Polar Substance" means a substance which has a formula weight between about 1,000 daltons and about 500,000 daltons, and an octanol/water partition coefficient less than about 1.0.

"Cargo" means a Large Polar Substance which is to be delivered into the cytosol or cytosol/nuclear compartment of animal cells.

A "delivery system" is the combination of reagents and procedures used to achieve delivery of a selected cargo into a desired compartment within a cell.

The "plasma membrane" is the outer lipid bilayer membrane encompassing the cell and in contact with the extracellular medium.

"Endocytosis" is the process of invagination and pinching off of the plasma membrane to form an enclosed vesicle (an endosome) within the cytosolic compartment of the cell, with that endosome being subsequently acidified by proton pumps embedded in the endosomal membrane. This invagination process results in engulfment of substances bound to the outer face of the plasma membrane and/or substances present in the extracellular medium.

"Endocytosis" as used herein includes related processes, such as pinocytosis and potocytosis, that accomplish a similar engulfment followed by acidification.

"Endocytosis-mediated cytosolic delivery" means a delivery process wherein a selected cargo is first endocytosed, after which the cargo is released or transported from the endosome into the cytosol of the cell.

"Acidification of endosome" is a natural process whereby proton pumps embedded in the endosomal membrane act to reduce the pH of the contents of the endosome from an initial value of about 7.0 to 7.5 immediately following endocytosis to a final value in the range of about 5.0 to 6.0. Typically, when the pH drops to about 5 or slightly lower the endosome merges with or otherwise becomes a lysosome, wherein the acidic conditions serve to activate degradative enzymes effective to digest most cargo types (one exception being Morpholino antisense oligos which are completely resistant to degradative enzymes).

"Neutral pH" means the pH range typical of the extracellular medium and within the cytosol of animal cells, generally about pH 7.0 to 7.5.

"Acidic pH" means the pH range typical of the interior of late-stage endosomes, generally in the range of about pH 5.0 to 6.5.

"Strong-base amino acid" means an amino acid having a side chain which is largely cationic in aqueous solutions at neutral pH. The typical "strong-base amino acids" in peptides are lysine, having a side-chain primary amine, and arginine, having a side-chain guanidinium moiety.

"Weak-base amino acid" means an amino acid having a side chain which is largely non-ionic at neutral pH, but substantially cationic in aqueous solutions at acidic pH. The typical weak-base amino acid in peptides is histidine, having a side chain imidazole moiety.

"Acid amino acid" means an amino acid having a side chain which is largely anionic in aqueous solutions at neutral pH. The typical acid amino acids are glutamic acid and aspartic acid, each having a side chain carboxylate moiety.

"Mixed-base" is used herein to indicate a composition which contains multiple strong-base and weak-base moieties, of which at least 40% are of the strong-base type.

"Face" is used herein to indicate a cluster or group of amino acid side chains having similar properties, such as aliphatic moieties having high lipophilicity, where those side chains are clustered on the same side of the helical axis of a peptide existing in an alpha helical conformation. This is detailed in the following section and illustrated in FIGS. 4 and 5.

"Amphiphilic peptide" is used herein to indicate an alpha helical peptide which has two main faces, one face being lipophilic and the other face being relatively hydrophilic by virtue of polar side chains, which may be ionic at neutral and/or acidic pH.

"Co-engulfment" means an endocytosis process wherein both delivery peptide and cargo end up in the same endosome.

"Permeabilization" means disruption of a cellular lipid bilayer sufficient that a selected cargo can readily pass through that membrane.

"26-mer peptide" means a linear peptide 26 amino acids in length, corresponding to a 39 angstrom length when that peptide is in an alpha helical conformation.

"Morpholino antisense oligo" is a sequence-specific nucleic acid-binding oligomer composed of nucleobases, each linked to a morpholino backbone moiety, with all backbone moieties joined in a selected order via phosphorodiamidate intersubunit linkages (Summerton, 1999).

"Weak-base amphiphilic delivery peptide" means peptides of the instant invention, where each has a lipophilic face composed predominantly of lipophilic aliphatic amino acids, and a weak-base face composed predominantly of basic amino acids, with at least 70% of the amino acids of the weak-base face being histidines.

DETAILED DESCRIPTION OF PREFERRED EMBODIMENTS

I. Composition of Delivery Peptide

A. Evolution of the Peptide Design and Composition

Peptides were selected as the basic structural type to be used for designing the desired delivery agents because peptides allow the easy positioning of selected moieties at defined positions in space, such as amino acid side chains along an alpha helical backbone. Peptides are also readily prepared from a versatile set of commercially available building blocks, including a weak-base amino acid (histidine), strong-base amino acids (lysine and arginine), and a variety of lipophilic amino acids (particularly the aliphatic amino acids: leucine, isoleucine, and valine).

Initial work entailed purchase of poly-histidine and preparation of a set of defined-length oligo-histidines. However, testing of these all-hisitidine peptides demonstrated that neither poly-histidine nor defined-length oligo-histidines achieved significant delivery of a representative cargo, such as a Morpholino antisense oligo, into the cytosol of cultured animal cells. This result suggested that this lack of delivery activity might be due to inadequate binding of the all-histidine peptides to cell surfaces, said binding likely being the necessary first step for efficient endocytotic uptake. However, the obvious solution of adding many strong-base amino acids (lysines or arginines) to afford strong electrostatic binding to cell surfaces would resurrect the problem of cell toxicity.

It was then speculated that adequate binding to cell surfaces might be achieved without concomitant toxicity by incorporating a lipophilic face in the prospective delivery peptide. To this end a series of amphiphilic peptides were designed with both an aliphatic lipophilic face and a weak-base face composed predominantly or completely of histidines. Aliphatic amino acid side chains were selected for the lipophilic face because earlier experimental results in designing strong-base delivery peptides suggested that aliphatic lipophilic faces give appreciably better membrane binding than do aromatic or mixed aromatic/aliphatic lipophilic faces. 11-Mer, 15-mer and 19-mer weak-base amphiphilic peptides were prepared. These lengths were selected because strong-base peptides, known to be effective for delivering substances into cells, are commonly in the 12 to 18 amino acid length range. Tests of these three weak-base amphiphilic delivery peptides with red blood cells showed that both a 15-mer and a 19-mer peptide with this type of structure appeared to bind, but not permeabilize, red blood cells at neutral pH, and to permeabilize red blood cells at pH 5, a pH value achieved within acidified endosomes. Such membrane binding without permeabilization at neutral pH, coupled with membrane permeabilization at acidic pH, was just the set of properties desired for an indirect endocytosis-mediated delivery agent.

While these initial experimental results with red blood cells appeared promising, subsequent testing of the peptides, each linked to a representative cargo (a Morpholino antisense oligo), showed that an 11-mer and a 15-mer weak-base amphiphilic peptide were only marginally effective for delivery. In contrast, the 19-mer peptide achieved reasonable delivery of a representative cargo into cells in serum-free medium, but achieved only minimal delivery in medium containing 10% serum, as shown in FIG. 2.

Despite these early inauspicious results in the presence of serum, continued development of the invention led to the weak-base amphiphilic delivery peptides of the instant invention, which are both non-toxic and quite effective in the presence of serum.

B. Faces of Delivery Peptide

In designing these weak-base amphiphilic delivery peptides, an alpha helix backbone structure was utilized in order to effectively position the various moieties relative to each other. This is achieved by incorporating amino acids known to favor an alpha helix conformation, and by avoiding amino acids known to disfavor or disrupt alpha helices (Chou, 1974). By designing for an alpha helix conformation, one can then readily select sequences having defined faces. This is based on the well-characterized structure of the peptide alpha helix wherein each amino acid side chain is rotated a constant 100 degrees about the helical axis relative to the previous amino acid side chain in the peptide. From this it can be seen that 3.6 amino acids give one full turn of the peptide backbone around its helical axis. To facilitate peptide design, side chain positions were plotted on a spiral graph wherein each successive numbered amino acid side chain is rotated 100 degrees about the helical axis relative to the previous amino acid of the chain, and each successive amino acid side chain is plotted a standard increment further out from the helical axis relative to the previous amino acid side chain in the peptide. Therefore, the axial distribution of a given amino acid side chain indicates its face position and its radial distance from the helical axis indicates its distance along the peptide chain.

Such an axial distribution plot is shown in FIG. 3, where the numbers indicate the relative positions of the consecutive amino acid side chains, both with respect to their axial distribution and their position along the length of the peptide chain.

Using this axial distribution plot, designing a two-face peptide simply entails selecting the number of degrees to comprise one of the faces. To illustrate, FIG. 4a shows a delivery peptide having a 200 degree lipophilic face and a 160 degree weak-base face. FIG. 4b shows a corresponding linear presentation of the sequence of this same delivery peptide. This linear presentation better illustrates consecutive alpha helical turns of the peptide.

To further illustrate pictorially, FIG. 5a shows a delivery peptide having a 160 degree lipophilic face and a 200 degree weak-base face. FIG. 5b shows the corresponding linear presentation of the same delivery peptide.

Experimental results suggest that delivery efficiency is relatively independent of whether the peptide sequence starts in the lipophilic or the weak-base face. It is also of little import whether the peptide sequence ends in the lipophilic or the weak-base face. Furthermore, it makes little difference whether the 1 position corresponds to the N-terminal or the C-terminal amino acid of the peptide.

In contrast to the above design flexibility, the respective sizes of the lipophilic and weak-base faces of the delivery peptide have a substantial impact on that peptide's delivery efficiency. This is illustrated by FIG. 6, which shows results from functional delivery assays of peptides with varying face sizes, both in the absence of serum (6a), and in the presence of 5% serum (6b). These assays utilized an established functional measurement of cytosolic delivery of a Morpholino antisense oligo in cultured cells (Kang, 1998). A representative test procedure of this type is described in Example 6, in a later section of his application.

The results of FIG. 6 show that reasonable delivery is achieved, both in the absence and presence of serum, when the weak-base face ranges in size from 180 to 220 degrees and the corresponding lipophilic face ranges from 180 to 140 degrees. These results also suggest that optimal delivery is achieved when the weak-base face is 200 degrees and the lipophilic face is 160 degrees. It is noteworthy that this highly-structured weak-base face, ranging in size from 180 to 220 degrees, differs greatly from the unstructured distribution of the weak-base moieties in the prior art peptide prepared by Midoux and coworkers, which reference is cited above (Midoux, 1998).

C. Amino Acid Composition of Delivery Peptide i. Lipophilic Face

In early unpublished work bearing on the design of these weak-base amphiphilic delivery peptides it was found that adequate lipophilicity is achieved when at least 80%, but preferably all of the amino acid side chains comprising the lipophilic face are both aliphatic and quite lipophilic. Thus, at least 80% of the amino acids comprising the lipophilic face should be selected from: leucine, isoleucine, norleucine valine and norvaline. Furthermore, no amino acid side chain in the lipophilic face should carry an ionic charge at neutral pH. The importance of using quite lipophilic side chains is illustrated by the fact that when leucines of the lipophilic face were replaced by alanines, the resultant peptide had little affinity for cell membranes, and even at pH 5 it was relatively ineffective for permeabilizing red blood cell membranes.

While the lipophilic face can be comprised of leucine, isoleucine, norleucine, valine and norvaline, the preferred amino acid for the lipophilic face is leucine. While isoleucine and valine give delivery peptides with good delivery efficiencies, leucine is preferred over these because its lesser steric hinderance about the alpha carbon results in better coupling efficiencies during peptide synthesis, resulting in lower production costs. While norleucine and norvaline also give delivery peptides with good delivery efficiencies, leucine is preferred over these because norleucine and norvaline are unnatural (not generally present in biological systems) amino acids which have the potential of causing toxicity in treated cells due to degradation of the delivery peptide within the cell and reutilization therein of its component amino acids.

ii Weak-base Face

To assure good delivery efficiency, at least 80% of the amino acids comprising the weak-base face should have a basic side chain which is protonated at acidic pH. Such amino acids include histidine, lysine and arginine. Furthermore, none of the amino acids of the weak-base face should contain an acidic side chain, such as is present in glutamic and aspartic acids.

Weak-base amphiphilic peptides where the weak-base face is all histidines have poor solubility in aqueous solutions at neutral pH. In an attempt to improve their aqueous solubilities, and possibly also to increase their cell binding properties, amphiphilic peptides were prepared wherein an increasing number of the histidines of the weak-base face were replaced by strong-base lysines.

FIG. 7 shows that for a 33-mer weak-base amphiphilic peptide containing 16 histidines, replacing one or two histidines, which are not ionized at neutral pH, with lysines, which are ionized at neutral pH, affords little improvement in aqueous solubility. However, replacing three histidines with lysines is seen to give moderate aqueous solubility at neutral pH (estimated at 2 microMolar), and replacing four or more histidines with lysines is seen to give much better aqueous solubility.

As shown in FIG. 8a, which is a functional assay of cytosolic delivery as described in Example 6, wherein the cargo was not linked to the delivery peptide, the replacement of three histidines with lysines, sufficient to give moderate aqueous solubility for the delivery peptide, gave somewhat reduced delivery efficiency relative to the corresponding delivery peptide with an all-histidine face.

In contrast, as shown in FIG. 8b, when the cargo was linked to the delivery peptide via a link designed to be cleaved within the cell and extra unlinked delivery peptide added, a functional assay of cytosolic delivery showed that replacement of three histidines with lysines gives a substantial increase in delivery efficiency relative to the corresponding delivery peptide with an all-histidine face.

These and other experimental results, combined with observations of treated cells, suggest that weak-base amphiphilic delivery peptides can be both effective and non-toxic when up to, but not more than 30% of the amino acids of the weak-base face are of the strong-base type. It should be appreciated that no more than about 30% of the amino acids should be of the strong-base type because amphiphilic peptides having weak-base faces with a higher percent of strong-base amino acids have been seen to cause a significant release of hemoglobin from red blood cells at pH 7.2, as described in Example 5. They can also inhibit the growth and division of cultured cells, as well as cause morphological changes suggesting toxicity to the treated cells.

To avoid toxic effects when a few strong-base amino acids are present in the weak-base face, it is important to properly distribute those strong-base amino acids to avoid toxicity to the treated cells. This is achieved by widely dispersing those few strong-base amino acids among the many weak-base histidines. More specifically, no more than one strong-base amino acid should be present in any two consecutive alpha helical turns of the peptide, and preferably no more than one strong-base amino acid should be present in any three consecutive alpha helical turns of the peptide. To illustrate, FIG. 9 shows unacceptable, acceptable, and preferred distributions of three strong-base amino acids along the length of a 26-mer weak-base amphiphilic delivery peptide.

To summarize: delivery results, observations of toxicity, and other considerations suggest that the weak-base face of these amphiphilic delivery peptides should contain at least 80% basic amino acids selected from histidine, lysine, and arginine, and at least 70% of the amino acids of that weak-base face should be histidines. Furthermore, the weak-base face should not contain any amino acids with acidic side chains (glutamic and aspartic acids).

iii. Chirality.

A weak-base amphiphilic delivery peptide can be assembled from all D amino acids or from all L amino acids, but it should not be assembled from a mixture of both D and L amino acids. This is because a mixture of both D and L chiralities disrupts the alpha helix used to properly structure and position the lipophilic and weak-base faces of the peptide. While all-D and all-L peptides afford essentially the same delivery efficiencies, for most applications the use of all-L amino acids, which is the chirality found in natural proteins, is preferred because after the peptide has carried out its delivery job, it can then be degraded into innocuous natural amino acids suitable for reuse by the cell.

D. Length of Delivery Peptide

While strong-base delivery peptides reported in the scientific literature are commonly in the 12 to 18-amino acid length range, early test results indicated that 11-mer, 15-mer, and 19-mer peptides of this new weak-base amphiphilic peptide type afforded little delivery in the presence of serum. In an effort to understand why serum might be inhibiting delivery, it was speculated that in the presence of serum the delivery peptide might be inserting into one of the hydrophobic clefts of serum albumin which commonly serve to transport fatty acids. If this were the case, then making the peptide substantially longer than the albumin cleft is deep might serve to extend a portion of the peptide out of the cleft sufficient to allow effective binding to proximal cell surfaces. It was also speculated that delivery peptides might achieve greater activity if they were at least as long as the plasma membrane is thick (about 36 angstroms, which corresponds to an alpha helix 24 amino acids long), thereby affording the possibility of a "staves in a barrel" type of membrane permeabilization mechanism. In light of these possibilities, a length series of these weak-base amphiphilic delivery peptides was prepared to test whether peptides longer than 19 amino acids might exhibit substantially improved delivery activity, including particularly delivery in the presence of serum.

FIG. 10 shows representative delivery efficiencies in cultured cells as a function of peptide length for peptides varying in length from 11 amino acids through 40 amino acids. The results shown in FIG. 10 suggest that weak-base amphiphilic delivery peptides with lengths ranging from about 19 amino acids to about 37 amino acids give reasonable delivery efficiencies, with peptide lengths of about 22 to 33 amino acids giving the best delivery efficiencies, particularly in the presence of serum.

E. C-Terminal Structure of Delivery Peptide

Typically, natural and most synthetic peptides contain a carboxyl moiety on the C-terminus (pKa commonly around 3.5 to 4.0) which is negatively charged at both neutral pH and at the acidic pH within endosomes. In view of the likely mechanism by which weak-base amphiphilic delivery peptides permeabilize endosomal membranes, it was postulated that converting the anionic C-terminus to a non-ionic amide might improve delivery efficiency.

FIG. 11 shows C-terminal structures of two identical-sequence peptides. One peptide has the typical anionic carboxyl, and the other peptide has an amide moiety which is non-ionic at both neutral pH and the acidic pH within endosomes. The lower portion of FIG. 11 shows measured delivery efficiencies for these two peptides. These and similar results indicate that rendering the C-terminus of the delivery peptide non-ionic affords a substantial increase in delivery efficiency.

F. N-Terminal Structure of Delivery Peptide

Usually, natural and most synthetic peptides contain an amine moiety on the N-terminus (pKa commonly around 8 to 9) which is positively charged at both neutral pH and at the acidic pH within endosomes. In view of the detrimental impact a negative charge on the C-terminus has on delivery efficiency, a test was also run to see if rendering the N-terminus non-ionic (by acylation) had a significant impact on delivery efficiency.

FIG. 12 shows N-terminal structures of two identical-sequence peptides. One peptide has the typical N-terminal primary amine, and in the other peptide that amine has been acetylated to give an amide moiety which is non-ionic at both neutral pH and the acidic pH within endosomes. The lower portion of FIG. 12 shows measured delivery efficiencies for these two peptides. These results suggest that rendering the N-terminus of the delivery peptide non-ionic has little effect on delivery efficiency.

II. Preparation of Delivery Peptide

Methods for preparing peptides, including the weak-base amphiphilic delivery peptides of the instant invention, are well known in the art, and highly refined peptide assembly methods are widely described in the scientific literature. They are also available from commercial sources such as the Nova Biochem Handbook and Catalog (Nova Biochem is an affiliate of Merck, KGaA, Darmstadt, Germany). In addition, a number of commercial entities will prepare specified custom-sequence peptides on request at reasonable prices.

In addition to the above generic methods for preparing peptides, Example 2 describes a method for preparing weak-base amphiphilic peptides of the instant invention, where those peptides have the preferred C-terminal amide structure.

Furthermore, Example 3 describes a method for linking a delivery peptide of the present invention to a representative cargo via a disulfide bond. That disulfide link is relatively stable outside of cells, but can be cleaved by components of the cell after delivery into cells.

III. Use of Delivery Peptide

A. Cargo Suitable for Delivery

A key question for any cellular delivery system is: what is the largest size of cargo that can be delivered? To answer this question, fluorescent tagged dextrans of varying sizes (approximate molecular weights of 3,000, 10,000, 40,000, 70,000, and 500,000) were contacted with animal cells along with the delivery peptide of the instant invention. More specifically, the delivery peptide was a 26-mer having a 200 degree weak-base face comprising 14 histidines and having a C-terminal amide. Dextrans of all sizes tested appear to be endocytosed. However, those dextrans which are too large to pass through the permeabilized endosomal membrane will remain trapped within endosomes; said trapping commonly shows as a perinuclear punctate pattern when viewed via fluoresence microscopy (the same pattern commonly seen when no delivery peptide is used). Conversely, dextrans of a size which can pass through the permeabilized endosomal membrane become dispersed throughout the cytosol. It should be noted that relatively small cargos (up to about 50,000 molecular weight) typically can pass through the nuclear pores and so can disperse throughout both the cytosol and nucleus, which together are referred to as the cytosol/nuclear compartment. Such dispersion due to escape from the endosomes shows as a diffuse fluoresence when viewed via fluoresence microscopy.

Results of these tests with fluorescent-tagged dextrans suggest that dextrans of at least 70,000 molecular weight can pass through endosomal membranes permeabilized by this delivery peptide. Corresponding tests with the 500,000 molecular weight dextran gave ambiguous results. Because such large cargos (at least 70,000 molecular weight, but possibly up to or over 500,000 molecular weight) appear to be deliverable with these weak-base amphiphilic delivery peptides, the composition and method of the instant invention can be used for delivering a wide variety of cargos. Such cargos include low molecular weight polar drugs and other biologically active substances, peptides and at least small to moderate size proteins, as well as oligonucleotides of various types, such as antisense DNA and RNA, ribozymes, and small interfering RNAs and related RNAs. The delivery peptides may also be effective for delivering condensed forms of mRNAs, plasmids and other polynucleotides. The delivery peptides of the instant invention are particularly effective for delivering advanced types of non-ionic antisense oligos, including Morpholinos and Peptide Nucleic Acids.

It should also be noted that the delivery peptide is fully capable of simultaneously delivering mixed cargo composed of multiple different types of large polar substances.

B. Linking Delivery Peptide to Cargo

The delivery peptide of the instant invention is generally quite effective when a mixture of cargo and delivery peptide is added to cells. However, in some cases it is desirable to covalently link one or multiple delivery peptides to the cargo. Because the delivery peptide has a substantial affinity for membranes, and because it is generally desired that delivered cargos be free to diffuse throughout the cytosol, when delivery peptide is to be linked to a cargo, that linkage should generally be of a type which is readily cleaved within cells. Representative cleavable links include an ester (cleaved by esterases), and more preferable, a disulfide (cleaved by glutathione).

A number of methods are known in the art for forming suitable links, including particularly disulfide links, and these are well described in Bioconjugate Techniques (Hermanson, 1996). In addition, Example 3 of the instant invention describes a method for linking a delivery peptide to a representative cargo comprising a Morpholino antisense oligo. This example illustrates a method for linking the cargo to the N-terminus of the delivery peptide. It should be appreciated that cargo can also be linked to the C-terminus of the delivery peptide, particularly by utilizing an initial disulfide linker on the synthesis resin, and after the peptide has been synthesized cleaving that peptide from the resin by reducing the disulfide link to the resin, and then using the resultant sulfhydral moiety for forming a new disulfide link to the cargo.

C. Formulation of Delivery Peptide

Delivery peptides whose weak-base faces are composed of about 80% to 100% histidines are typically poorly soluble in aqueous solutions at neutral pH. Accordingly, it is desirable to prepare such delivery peptides as an easily used stock delivery solution wherein the delivery peptide is fully dissolved, preferably at a concentration of about 1 to 3 milliMolar. Preparation of several effective stock solution formulations are described in Example 4.

The following have been found suitable for preparing stock solutions of delivery peptides.
  a. 20% water/80% ethanol
  b. 150 milliMolar aqueous sodium chloride (NaCl) plus 1 equivalent of acetic acid per equivalent of side chain base in delivery peptide
  c. 300 milliMolar aqueous sorbitol, plus 1 equivalent of acetic acid per equivalent of side chain base in delivery peptide
  d. dimethylsulfoxide (DMSO)

Typically a 1.3 milliMolar solution of delivery peptide in dimethyl sulfoxide constitutes a stable, effective, reliable, and easy to use formulation.

It has been found that for delivery into cells in culture a stock solution of 1 to 3 milliMolar delivery peptide in dimethyl sulfoxide gives particularly good results. This may be because in dimethyl sulfoxide the delivery peptide is fully in the monomeric state and, on dilution into 100 volumes of aqueous culture medium, the delivery peptide quickly forms large irregular aggregates. These aggregates contain exposed lipophilic faces which are quite effective in binding to cell surfaces. However, that 100 fold dilution of the dimethyl sulfoxide stock solution gives a final dimethyl sulfoxide concentration of about 1% in the culture medium and such a concentration of dimethyl sulfoxide is somewhat detrimental to some sensitive cell types. To remedy this, it has been determined that a stock solution of about 1 to 3 milliMolar delivery peptide in a mixture of dimethyl sulfoxide and water, ranging from about 15% DMSO/85% water to about 60% DMSO/40% water, and preferably about 30% DMSO/70% water to about 40% DMSO/60% water, still gives quite effective delivery while greatly reducing any detrimental effect of the dimethyl sulfoxide on sensitive cell types.

D. Delivery of Cargo Not Linked to Delivery Peptide

For cultured cells, a variety of cargos are readily delivered by mixing an appropriate amount of cargo with the cells and then adding an appropriate amount of stock delivery solution composed of delivery peptide dissolved in a suitable solvent, immediately followed by swirling to mix.

Typically, the desired final concentration of added cargo is dependent on the specific cargo used. Thus, appropriate amounts of cargo to be added should be determined empirically. In this invention, one representative cargo, a Morpholino antisense oligo, gives good results when added at a final concentration in the 0.2 to 5 microMolar range.

When no serum is present in the medium, delivery peptide at a final concentration in the range of about 6 to 15 microMolar in the cell culture generally gives good delivery of cargo. However, when serum is present a higher concentration of delivery peptide in the cell culture (typically from about 10 to 20 microMolar) generally gives good delivery efficiency, With most other delivery systems it is advisable to remove the delivery reagent after a relatively brief period of time, typically ranging from about 30 minutes to 3 or 4 hours, in order to limit toxicity to the treated cells. In contrast, because of the virtual lack of toxicity of the weak-base amphiphilic delivery peptides of the instant invention, the medium containing cargo and delivery peptide may be left in contact with the cells for hours to days, with only the need to refresh the culture medium being a factor in deciding when to remove the delivery peptide.

When the solvent used for making the stock delivery peptide solution (such as dimethyl sulfoxide) does not affect the integrity of the cargo, an appropriate amount of cargo may be added to a suitable volume of stock delivery solution and then that mixture added to cells and swirled to give the desired final concentrations of cargo and delivery peptide in the cell culture. An example of such a pre-mix procedure is described in Example 6.

E. Delivery of Cargo Linked to Delivery Peptide

Many prospective cargo types have little or no affinity for the outer surface of cells. In such cases only cargo in the extracellular medium immediately adjacent to the site of membrane invagination is co-engulfed with the delivery peptide. As a consequence, the amount of often-very-expensive cargo endocytosed along with the delivery peptide can be less than desired. The amount of cargo endocytosed with the delivery peptide can be substantially increased by linking the cargo to the delivery peptide via a linkage type which will be cleaved within the cell, such as a disulfide link. By this means the linked delivery peptide acts to concentrate the cargo at the plasma membrane, thereby considerably increasing the amount of cargo co-engulfed with delivery peptide during endocytosis.

For many cargos an appropriate final concentration in the medium is 1 microMolar or less, particularly when its endocytosis rate has been considerably increased by virtue of an attached delivery peptide. In contrast to the relatively low concentrations appropriate for many cargos, concentrations of delivery peptide which give good delivery efficiency are commonly in the range of about 6 to 20 microMolar. It has been found that such different concentration requirements for cargo and delivery peptide can be accommodated by using an appropriate concentration of cargo to which is linked delivery peptide, and then adding extra non-linked delivery peptide to give the total concentration of delivery peptide (ie., linked to cargo plus non-linked) optimal for maximum cytosolic delivery. Alternatively, for large cargos multiple delivery peptides can be linked to each molecule of cargo.

F. Delivery of Cargo In Vivo

An obvious application of the delivery peptide of the instant invention is its use for delivering cargo into the cytosol of cells in living animals, including humans. Example 8 describes a preliminary assessment of the ability of a weak-base amphiphilic delivery peptide to deliver a representative cargo into cells in living mice.

G. Improved Formulation for In Vivo Applications:

In order for delivery peptide to be effective in delivering cargos into most cells in the body that delivery peptide must pass through capillary walls. It is known that for most capillaries the composite size of the substance to pass through those walls must generally be smaller than the size of an albumin molecule (69,000 daltons). When a delivery peptide having mostly or only leucines on the lipophilic face and mostly or only histidines on the weak-base face is formulated as described in Section III. C., on introduction into an aqueous medium, such as blood, that peptide appears to form large aggregates which are far too large to pass through most capillary walls.

Applicant has discovered that when a neutral aqueous suspension of such a delivery peptide is heated to greater than about 50 deg. C., and preferably sterilized at about 120 deg. C., that the peptide goes into solution. On slow cooling (over a period ranging from about 2 to about 20 minutes) the delivery peptide appears to form defined complexes which remain soluble indefinitely if the salt concentration is low (less than about 50 milliMolar). Such water-soluble forms of delivery peptides probably comprise complexes of from about 2 to 4 molecules, but mostly three molecules of delivery peptide in each complex. In these multi-stranded peptide complexes the lipophilic faces are likely in the interior of the complex and the weak-base faces are on the exterior of the complex. Preliminary tests in mice, described in Example 9, suggest that such complexes (expected to have molecular masses of about 10,000 daltons) can indeed pass through capillary walls and achieve delivery of a Morpholino antisense oligo into the extra-capillary cells of mice.

Preferred stock solution formulations for in vivo use, and for use with cultured cells where dimethyl sulfoxide would be problematic, can be made by dispersing dry delivery peptide (sufficient to give a 1 to 3 milliMolar concentration in the stock solution) in an aqueous solution which is low in salt (less than about 50 milliMolar) and near isotonic (between about 0.2 and about 0.4 Osmolar). An aqueous solution 0.3 Molar in mannitol or sorbitol is particularly preferred. The container is tightly capped and heated at 120 deg. C. for about 15 minutes, shaken vigorously to assure all particulates are dissolved, and heated for about another 15 minutes. The hot solution is then placed in a Styrofoam container, covered, and the solution of delivery peptide allowed to slowly come to room temperature over a period of about 20 minutes. This gives a sterile isotonic solution ready for use in vivo. As described in Example 9, one then simply adds an appropriate volume of this delivery peptide solution to an appropriate amount of cargo and injects the mixture into the organism to be treated.

IV. EXAMPLES

Example 1

Designing Weak-base Amphiphilic Peptides Using Axial Distribution Plots

When designing amphiphilic alpha helical peptides where each face is to carry out a distinct function, it is useful to visualize the positioning of the various side chain types, both around the helical axis and along the length of the peptide chain. While this can be accomplished by molecular modeling, such modeling is relatively slow and requires a large investment of resources in order to allow easy comparisons between multiple peptides.

In contrast, by plotting side chain positions of a peptide on the spiral axial distribution plot illustrated in FIG. 3, one can rapidly and easily visualize and compare the key side chain distributions for large numbers of peptides. This is illustrated in FIG. 13 wherein the semi-natural weak-base delivery peptide of Midoux (in the 1998 specific reference cited supra) is compared to a representative designed-from-scratch weak-base amphiphilic delivery peptide of the instant invention.

As seen in FIG. 13a, in the semi-natural peptide of Midoux (1998) (prior art) four face types would be discernable if this peptide were to exist in a regular alpha helical conformation. However, this peptide contains 6 glycines distributed along the length of the peptide (positions 1, 12, 13, 16, 20, and 23), and because glycines disfavor an alpha helical conformation it is very unlikely that this peptide exists in a structured alpha helical conformation. Thus, in regard to conformation, the unstructured prior art weak-base peptide of Midoux differs greatly from the highly-structured alpha-helical amphiphilic delivery peptides of the instant invention, such as illustrated in FIG. 13b.

Example 2

Synthesis and Processing of Delivery Peptides

Delivery peptides with the standard anionic C-terminus were made on the Wang resin and assembled by an automated peptide synthesizer using fluorenylmethoxycarbonyl-protected/pentafluorophenyl ester-activated amino acids. Deprotection and cleavage from the resin was with triisopropylsilane/water/trifluoroacetic acid by methods well known in the art (NovaBiochem Handbook and Catalog, 2000).

Synthesis of delivery peptides with the preferred C-terminal amide were made on a hydroxymethyl polystyrene resin (100–200 mesh, 1% x-linked, 0.82 milliMoles/g, Catalog # 01-64-0110 from NovaBiochem). After assembly by an automated peptide synthesizer using fluorenylmethoxycarbonyl-protected/pentafluorophenyl ester-activated amino acids, followed by addition of any desired N-terminal moiety, the resin/peptide preparation was washed well with dichloromethane and then suspended in 2% water/5% tri-isopropylsilane/30% dichloromethane/63% trifluoroacetic acid for 4 hours to cleave trityl groups from histidine side chains and t-butoxycarbonyl groups from any lysine side chains.

To cleave the peptide from the resin and generate the C-terminal amide, the resin was added to a fritted funnel and washed thoroughly with dichloromethane, dried, and then suspended in 33% methylamine/67% ethanol, the container was capped and incubated at 50 degrees C. for 2 hours. Next, the cleavage solution was filtered through a fritted funnel into a rotovap flask and the resin was washed thoroughly with trifluoroethanol, with that wash also being added to the rotovap flask. Rotary evaporating ("rotovaping") in a 50 degree C. water bath removed the methylamine, ethanol, and trifluoroethanol. The peptide residue was dissolved in a minimal volume of methanol and then precipitated by rapid addition of about 30 volumes of t-butylmethylether.

After mixing well for 5 minutes the preparation was centrifuged or filtered. The peptide was again dissolved in a minimal volume of methanol and precipitated with t-butylmethylether and the precipitated peptide collected and dried under vacuum. These peptides are generally suitable for use without further purification.

Typically the mass of each peptide is confirmed by disolving about 0.1 mg in 50 microliters of methanol, and then running a matrix assisted laser desorption ionization time of flight mass spectrum, where the matrix is sinapinic acid.

Generally, the delivery peptides of the instant invention are non-hydroscopic and can be stored at room temperature and open to the atmosphere for long periods of time with no significant degradation.

Example 3

Covalent Linking of Delivery Peptide to Cargo

When the delivery peptide is to be linked to the cargo, the preferred linkage type is a disulfide bond. A variety of methods for linking one molecule to another via a disulfide bond are well known in the art, such as described in Bioconjugate Techniques (Hermanson, 1996).

The following is a procedure for coupling a delivery peptide of the instant invention to a representative cargo comprising a Morpholino antisense oligo. FIG. 14 illustrates key structures and reactions described in this procedure.

a) Preparation of Disulfide Linker Reagent (I)

Stir 20 milliMoles of 4,4'-dithiodibutyric acid and 50 milliMoles of p-nitrophenol in dichloroethane till disolved. Add 42 milliMoles of 1,3-diisopropylcarbodiimide, cover and let stand at room temp. 3 hr. Filter off solid (diisopropylurea) and purify diester product (I) on silica gel column eluted with dichloromethane. Precipitate product by adding hexane, collect by filtration and dry under vacuum.

b) Preparation of Delivery Peptide Component (II)

Following peptide assembly, as described in Example 2, but before deprotection of the side chains or cleavage from the resin, treat 50 mg of resin-peptide preparation in a fritted column with 20% piperidine/80% DMI (N,N'-dimethylimidazolidinone) to cleave off the N-terminal fluorenylmethoxycarbonyl protective group. Next, wash the resin-peptide thoroughly with DMI to remove all piperidine.

To resin-peptide bed in a fritted column add 0.25 ml of disulfide linker solution (50 mg of disulfide linker (I) in 0.48 ml of DMI) and allow to drain into bed. Cap the fritted column top and bottom and incubate at 50 degree C. for 1 hour. Uncap the column and add the remaining 0.25 ml of the disulfide linker solution and let drain into the column, cap the column top and bottom and incubate at 50 deg. another 3 hours. Wash the column with 2 ml of 10% morpholine in DMI, let stand at room temperature for 15 minutes, and then wash with DMI, then dichloromethane, and dry the resin-peptide preparation. Add this dried preparation to 15 ml of deprotection solution (2% water/5% triisopropylsilane/30% dichloromethane/63% trifluoroacetic acid), cap and shake periodically over the course of 4 hours at room temperature. This serves to deprotect histidine and any lysine and arginine side chains of the peptide.

Transfer the resin-peptide preparation to a fritted column and wash with dichloromethane, and then dry the resin-peptide under vacuum. Add the dried resin-peptide to a 20 ml vial and add 10 ml of cleavage solution (33% methylamine/67% ethanol), cap and let stand at room temperature for 4 hours to cleave the peptide from the resin and generate a C-terminal amide on the peptide.

Transfer the cleavage solution and resin to a fritted column positioned to drain into a rotovap flask. Use trifluoroethanol to complete the transfer and to wash all delivery peptide from the synthesis resin. Rotovap the combined cleavage solution and trifluoroethanol wash to dryness. Resuspend the peptide residue in a minimal volume of methanol and precipitate by adding about 30 volumes of t-butylmethyl ether. Collect the precipitate by filtering or centrifugation and dry. Cleave the disulfide of the attached linker (90 minutes at room temp. in 0.1 Molar dithiothreitol/0.3 Molar triethylamine in trifluoroethanol). Rotovap off the trifluoroethanol and then wash peptide by suspending it in a minimal volume of methanol and precipitating with t-butylmethyl ether, centrifuging, discarding the supernatant, and drying the pelleted peptide. Repeat this wash process once more.

To 5 microMoles of delivery peptide in 0.5 ml of trifluoroethanol add 40 microMoles of 2,2'dithiodipyridine dissolved in 0.5 ml of trifluoroethanol. After 2 hours rotovap off the trifluoroethanol, and wash the peptide by resuspending in a minimal volume of methanol and add to 48 ml of rapidly-stirred t-butylmethyl ether. Stir 10 minutes and centrifuge. Discard the supernatant and dry the pelleted peptide. Repeat this wash procedure two more times to remove the last traces of 2,2'dithiodipyridine, to give final delivery peptide component (II).

It should be noted that this delivery peptide component (II) can be coupled by methods well known in the art to virtually any cargo containing an available sulfhydral moiety.

c) Preparation of Cargo: Morpholino Antisense Oligo Component (III)

To a fritted column add a 1 microMole preparation of dry Morpholino antisense oligo still linked to its synthesis resin, with its nucleobases still protected, and with an unprotected 3' morpholine nitrogen (Summerton, 1997). Solvate with DMI. To the solvated resin-Morpholino bed add 0.25 ml of disulfide linker solution (50 mg of disulfide linker (I) in 0.48 ml of DMI) and allow to drain into bed. Cap the fritted column top and bottom and incubate at 50 degree C. for 1 hour. Uncap the column and add the remainder of the disulfide linker solution and let drain into the column, cap the column top and bottom and incubate at 50 deg. another 3 hours. Wash the column with DMI to remove excess linker, then dichloromethane, and dry the resin-Morpholino preparation.

To this dried preparation in a 2 ml screw cap vial add 0.6 ml of concentrated ammonium hydroxide, cap, and incubate 4 hours at 50 degrees C. to cleave the Morpholino oligo from its synthesis resin and deprotect the nucleobases. Filter the cleavage mix through a fritted column and wash the resin with 0.6 ml of water. Add the filtrates to 48 ml of acetone in a 50 ml centrifuge tube, cap and shake for several minutes and then centrifuge to pellet the Morpholino oligo with attached linker. Dry off the acetone under vacuum.

Cleave the disulfide of the attached linker (90 minutes at room temp. in 0.1 Molar dithiothreitol/0.3 Molar triethylamine in trifluoroethanol). Rotovap off the trifluoroethanol, suspend the Morpholino oligo in a minimal volume of methanol, and precipitate with t-butylmethyl ether. Wash the Morpholino oligo by resuspending in a minimal volume of methanol and add to 48 ml of rapidly-stirred t-butylmethyl ether. Stir 10 minutes and centrifuge. Discard the supernatant and dry the pelleted Morpholino oligo. Repeat this wash procedure two more times to remove the last traces of dithiothreitol, to give final Morpholino component (III).

d) Coupling Delivery Peptide Component (II) to Morpholino Antisense Oligo Component (III) to Give Disulfide-linked Delivery Peptide/Morpholino Oligo Product (IV)

Dissolve 2 microMoles of delivery peptide component (II) in 0.1 ml of trifluoroethanol. Disolve 1 microMole of Morpholino oligo component (III) in 0.1 ml of trifluoroethanol. Combine the two solutions, cap, and let stand at room temperature for 8 hours.

e) Purification of Disulfide-linked Delivery Peptide/Cargo Product (IV)

In a fritted column pour a 0.5 ml bed volume of Q Sepharose anion exchange resin (bead size 45 to 165 microMeters, 180 to 250 microEquivalents/ml, 4,000,000 dalton exclusion limit; catalog # Q-1126 from Sigma Chem. Co., Saint Louis, Mo.). In another fritted column pour a 0.5 ml bed volume of SP Sepharose cation exchange resin (bead size 45 to 165 microMeters, 180 to 250 microEquivalents/ml, 4,000,000 dalton exclusion limit; catalog # S-1799 from Sigma Chem. Co., Saint Louis, Mo.). Wash each column with 3 ml of water.

To the reaction mixture of delivery peptide and Morpholino oligo add 0.3 ml of trifluoroethanol/1 ml of water/0.02 ml of N-methylpyrrolidine (to ionize the G and T nucleobases of the Morpholino oligo), and pass this solution through the bed of Q Sepharose anion exchange resin. This serves to bind the Morpholino oligo, and any delivery peptide linked to Morpholino oligo. Wash the column with 0.33 ml trifluoroethanol/0.67 ml water to wash through any non-linked delivery peptide, and then elute Morpholino and Morpholino/peptide product with 3 ml of aqueous pH 5.2 buffer (0.02 M malic acid, adjust to pH 5.2 with 2 M NaOH).

Add this pH 5.2 eluant to the bed of SP Sepharose cation exchange resin, which serves to bind the peptide component of the Morpholino/peptide product, while allowing any non-linked Morpholino to pass through the column. Wash the column with another 2 ml of pH 5.2 buffer, then with 2 ml of water, followed by 2 ml of methanol, and finally elute the Morpholino/peptide product (IV) with 0.03 ml N-methylpyrrolidine/3 ml trifluoroethanol. Rotovap off the methylpyrrolidine and trifluoroethanol, suspend the residue in a minimal volume of methanol, and add to t-butylmethyl ether, mix well, centrifuge, discard supernatant, and dry the pelleted product (IV) under vacuum.

Example 4

Formulation of Delivery Peptides

Because delivery peptides are used in low microMolar concentrations and because they typically do not dissolve readily in neutral aqueous solutions, such peptides are most easily used by first preparing a concentrated stock solution in a suitable solvent. A small volume of this stock solution is then added to the much larger volume of culture medium containing the cells, followed by swirling to thoroughly mix the stock solution with the culture medium.

To prepare a stock solution of delivery peptide, weigh out a precise amount of thoroughly dried delivery peptide and then add a volume of solvent to give the desired concentration of delivery peptide. A stock solution 1 to 3 milliMolar in delivery peptide typically gives the best delivery efficiencies.

Stock solutions of delivery peptide where dimethyl sulfoxide is the solvent generally give the best delivery efficiencies. However, in cases where delivery peptide is linked to cargo, and the cargo would be denatured or otherwise damaged by dimethyl sulfoxide, it is desirable to use an alternative solvent for preparing the stock solution. Generally the second best solvent for stock solutions is aqueous 0.15 M NaCl containing 1 equivalent of acetic acid per equivalent of side chain base in the delivery peptide. Regarding this added acetic acid, if the stock solution is to contain a 1 milliMolar concentration of delivery peptide and that delivery peptide contains 14 histidines, then one would add acetic acid to a concentration of 14 millimolar. The third best solvent for stock solutions is aqueous 0.3 M sorbitol containing 1 equivalent of acetic acid per equivalent of side chain base in the delivery peptide. The fourth best solvent for stock solutions is 20% water/80% ethanol. Methanol is also an acceptable solvent for stock solutions, but stock solutions containing methanol are difficult to pipette accurately because of methanol's high vapor pressure.

Example 5

Use of Red Blood Cells for Assessing Membrane Binding and Permeabilization

Red blood cells can be used to easily, rapidly, and quantitatively assess a prospective delivery peptide's binding affinity for cell membranes, and to assess its ability to permeabilize cell membranes sufficient to allow passage of a moderate size protein, hemoglobin.

To assess a peptide's membrane binding affinity, a label having an absorbance wavelength well away from that of hemoglobin, such as fluorescein or rhodamine, is linked to the peptide, typically through the N-terminal amine of the peptide while it is still on its synthesis resin. That labeled peptide, at a concentration readily quantitated by spectrophotometry, is then mixed with red blood cells suspended in an isotonic saline solution (0.15 M NaCl) buffered to the desired pH (typically pH 5.0 or 7.2). After mixing and letting the mixture stand for a specified period of time, the red blood cells are centrifuged out and the amount of labeled peptide remaining in solution is assessed on a spectrophotometer. When the peptide has significant permeabilizing activity, it is important to run a control spectrum of released hemoglobin in order to correct for any absorbance contribution from hemoglobin released from the red blood cells by the peptide.

To assess a peptide's ability to permeabilize cell membranes the following procedure is used.

i) isotonic saline: Dissolve 8.7 g NaCl (0.15 mole) in 1000 ml distilled water.

ii) isotonic pH 5.0 buffer: To 100 ml of isotonic saline add 134 mg (1 milliMole) of malic acid and adjust to pH 5.0 using aqueous 2 M NaOH.

iii) isotonic pH 7.2 buffer: To 100 ml of isotonic saline add 209 mg (1 milliMole) of 3-(N-morpholino)propane acid and adjust to pH 7.2 using aqueous 2 M NaOH.

iv) isotonic red blood cell (RBC) suspension:

Prick finger with a sterile lancet and collect about 10 drops of blood into a 15 ml centrifuge tube containing 14 ml of isotonic saline. Mix well, centrifuge and draw off supernatant. To pelleted RBCs add 14 ml of isotonic saline, mix well, centrifuge and draw off supernatant. Repeat this wash process one more time. To pelleted RBCs add 0.4 ml of isotonic saline, mix thoroughly, and add 10 microLiters of this RBC suspension to 990 microLiters of water to cause osmotic lysis and release of hemoglobin from cells. Mix well and scan from 600 to 300 nm in spectrophotometer. Use the absorbance value at 414 nm to calculate how much the RBC suspension should be diluted with isotonic saline in order to give an absorbance of about 2.0 at 414 nm if all the hemoglobin is released from the RBCs. Dilute the RBC suspension with isotonic saline the calculated amount. Store this final stock RBC suspension in an ice bath during the course of the experiments and use on the day the RBC suspension was prepared.

V) Procedure for assessing membrane permeabilization

To a 2-ml centrifuge tube add 15 microLiters of a 1.3 milliMolar stock solution of delivery peptide. Forcefully pipette in 1 ml of selected isotonic buffer to rapidly disperse the concentrated stock peptide solution, followed by addition of another 0.47 ml of the same isotonic buffer. Next, add 15 microLiters of the isotonic RBC suspension. Cap, mix by inverting the tube three times, and then let stand at room temperature for 30 minutes. Centrifuge, preferably in a swinging bucket rotor, to pellet the RBCs. Next, carefully take 1 ml of supernatant from the upper portion of the tube and assess its absorbance at 414 nm to quantitate the amount of released hemoglobin. For the 100% release value do an identical preparation, except use water instead of isotonic buffer. For the no release value do an identical preparation, except instead of the stock peptide solution, use only the solvent used to make the stock peptide solution (typically dimethyl sulfoxide).

In the above tests, the weak-base amphiphilic delivery peptides of the instant invention generally give little or no hemoglobin release in the pH 7.2 buffer, but give much or complete hemoglobin release in the pH 5.0 buffer. Further tests with lower concentrations of delivery peptide and/or shorter incubation times and/or at pH 6 serve to give one an estimate of the relative delivery efficiencies to be expected for various peptide sequences and modifications. It should be noted that peptides which release substantial hemoglobin at pH 7.2 are generally found to be somewhat toxic to cells.

Example 6

Functional Quantitative Assessment of Cytosolic Delivery of a Representative Cargo in Cultured Animal Cells The most definitive assessment of cytosolic delivery is one wherein when a cargo is delivered into the cytosol of a cell it generates a quantifiable signal proportional to the amount of cargo delivered into the cytosol. Also, for definitive results, that cargo should be completely stable within the cytosol so that increases due to delivery are not underestimated due to losses from degradation.

The splice-correction system developed by Kole and co-workers (Kang, 1998), coupled with a Morpholino antisense oligo (which is completely stable within cells) targeted against the splicing error site, has been found to satisfy these requirements for quantitative assessment of cytosolic delivery. In the Kole test system (commercially available from GENE TOOLS, LLC, Philomath, Oreg.) a cell line has been stably transfected with a gene that codes for an RNA transcript that includes a mutation that generates a splicing error which acts to prevent the translation of luciferase coded by that RNA transcript. When a properly-targeted Morpholino antisense oligo (commercially available from GENE TOOLS, LLC, Philomath, Oreg.) is delivered into the cytosol/nuclear compartment of such cells, the Morpholino blocks the mutant site. This leads to normal translation of the luciferase, and the light emission from that luciferase is readily quantitated in a luminometer.

The following is a typical assay for cytosolic delivery using the above functional assay system:

i) Seed the transfected cells in a 75 cm tissue culture flask and allow cells to grow to confluency;

ii) Split the cells into 24-well plates and allow cells to grow to 80% confluency in 1 ml in each well of DMEM-F12 media (Catalog # 11330-032, Gibco BRL, Gaithersburg, Md.) and 5% fetal bovine serum;

iii) On the day of the experiment, replace the culture medium with fresh medium of the same type;

iv) To the test well add a suitable volume of stock solution of the cargo to give the desired final concentration of cargo in the culture well. For Morpholino antisense oligo this is typically 1 microLiter of a 1 milliMolar stock solution of Morpholino oligo in water; giving a final 1 microMolar concentration of Morpholino oligo in the well;

v) Swirl briefly to mix;

vi) Next, add a suitable volume of stock solution of delivery peptide to give the desired final concentration of delivery peptide. For optimal delivery of Morpholino antisense oligos this is typically about 10 microLiters of a 1.3 milliMolar stock solution of delivery peptide in dimethyl sulfoxide;

vii) Immediately after adding the stock solution of delivery peptide swirl the plate to mix.

An alternative to the above sequential addition of cargo and delivery peptide is to use a premix procedure. This entails mixing 1 volume of the 1 milliMolar stock Morpholino solution and 10 volumes of the 1.3 milliMolar stock delivery peptide solution, and then adding 11 microLiters of this mixture to the test well of cells, and immediately swirling to mix. While this premix procedure gives the same final concentrations of cargo and delivery peptide as above, it has been found to give somewhat greater delivery (typically about a 20% to 30% increase) than achieved by the sequential addition procedure.

After addition of the cargo and delivery peptide, return the culture plate to the $CO_2$ incubator and incubate at 37 degrees C. for the desired delivery time. Because the delivery peptides of the instant invention are virtually non-toxic to the cells, incubation is typically carried out for 18 hours, after which the cells are lysed and assayed for both luciferase and total cell protein. Quantitation of luciferase in the cells treated with Morpholino antisense oligo and delivery peptide entails lysis of the cells with Glo Lysis Buffer (Catalog # E2661, Promega, Madison, Wis.) and then adding 10 microLiters of that cell lysate to 40 microLiters of solution from the Steady-Glo Luciferase Assay System (Catalog # E2520, Promega, Madison, Wis.), mixing 5 seconds and then monitoring light emission for 10 seconds.

Quantitation of protein from the cells is carried out by adding 10 microLiters of the above cell lysate to 990 microLiters of a 5-fold dilution of protein dye from the Bio-Rad Protein Assay Kit (Catalog # 500-0001, Bio-Rad Laboratories, Hercules, Calif.), and then measuring Absorbance at 595 nm.

To correct for variations in cell density from well to well in the culture plate, light emission values are divided by protein absorbance values to give normalized luciferase values, which serve as a measure of cytosolic delivery.

Example 7

Assessments of Toxicity in Treated Cells

Several currently popular methods for assessing damage to cells entail adding to the cell culture polar and/or ionic substances which do not readily enter the cytosol or nucleus of an animal cell unless the plasma membrane of that cell is damaged. Such substances include the vital dyes, and more recently, ionic dyes such as ethidium homodimer which only become fluorescent when intercalated into duplex DNA in the nucleus of the cell.

It should be appreciated that such substances are not suitable for assessing cell toxicity in the presence of delivery peptides and other delivery reagents. This is because, at least for the case of delivery peptides of the instant invention, the delivery peptide is explicitly designed to deliver just such types of substances into the cytosol/nuclear compartment of cells, but by an indirect endocytosis-mediated mechanism which avoids compromising the integrity of the plasma membrane of the cell. As a consequence, vital dyes and ionic DNA-intercalating agents generally give a false indication of toxicity for such advanced delivery peptides.

One suitable method for assessing cell toxicity due to exposure to delivery reagents is to assess for release from the cell of large polar substances which are normally restricted to the cytosol/nuclear compartment of the cell. For instance, toxicity to cells expressing beta galactosidase can be readily monitored by assessing release of this enzyme into the culture medium due to damage to the plasma membrane of the cell.

An alternative, very simple and more rigorous method for estimating cell toxicity due to the presence of a delivery agent is to plate cells at low to medium cell density into a number of wells of a 24-well culture plate. Half of the wells are then treated with an appropriate concentration of the delivery reagent, and the other half of the wells serve as the untreated controls. After a suitable treatment period, such as 18 to 36 hours, the cells in each well are washed three times with serum-free medium, and then lysed as described in Example 6, and the protein in each lysate quantitated using the Bio-Rad Protein Assay Kit, as also described in Example 6. Delivery agents which are toxic to the treated cells cause a marked reduction in cell growth, resulting in substantially reduced protein concentrations in the final cell lysates, relative to the lysates from the untreated control wells.

Using such a toxicity assay, it is commonly found for many delivery agents that the cells are completely killed over the course of an 18 hour exposure, while effective concentrations of the delivery peptides of the instant invention generally have little or no effect on cell growth and division, particularly when a few percent of serum is present.

Example 8

Use of Delivery Peptide to Deliver Cargo In Vivo

Kole and coworkers have developed a strain of transgenic mice carrying an expressed gene that codes for an RNA transcript that potentially codes for a green fluorescent protein (Sazani, 2002). That RNA transcript contains a mutation that causes a splicing error which prevents expression of the green fluorescent protein. Contacting an appropriate Morpholino antisense oligo with that mutant RNA transcript has been shown to block that mutant site, thereby correcting the splicing error and generating green fluorescent protein. Thus, successful cytosolic delivery into cells of a tissue in vivo should lead to easily visualized green fluorescence in that tissue.

To assess the ability of the instant invention to achieve cytosolic delivery in vivo, a Morpholino antisense oligo was linked to a delivery peptide via a disulfide bond. That cargo-peptide construct was then formulated at a concentration of 1 milliMolar in isotonic saline with 1 equivalent of acetic acid added per equivalent of basic side chain in the delivery peptide. This formulated product was injected into the tail vein of several of the mice of the transgenic strain developed by Kole.

Modest levels of fluorescence, indicative of cytosolic delivery, were seen in tissues of the treated mice, particularly in the lungs and liver.

Example 9

Use of Delivery Peptide with Improved Formulation to Deliver Cargo In Vivo

A delivery peptide having a length of 26 amino acids, a 160 deg. lipophilic face of all leucines, and a 200 deg. weak-base face of all histidines was suspended in 0.3 M aqueous sorbitol to give a suspension with a peptide concentration of 1.3 milliMolar. This non-ionic, isotonic solution was then tightly capped and heated at 120 deg. C. for 15 minutes, shaken briefly to effect complete dissolution of the peptide, and then heated for another 15 minutes. The stock solution of delivery peptide was then placed in a Styrofoam box, covered with a lid, and the peptide solution allowed to slowly come to room temperature.

A portion of the sterile isotonic stock peptide solution was added to sterile freeze-dried Morpholino antisense oligo targeted against the splice mutation site described in Example 8 to give a solution 1.0 milliMolar in Morpholino oligo and 1.3 milliMolar in delivery peptide. Varying volumes of this composite solution were injected into the tail vein of transgenic mice, as described in Example 8, daily for 3 days. Subsequent assessment of various tissues from those mice using reverse transcriptase and polymerase chain reaction amplification demonstrated that a portion of the splice mutation sites in the targeted RNA transcripts had been corrected. This indicates successful delivery of the Morpholino into the cytosol of the mouse cells in vivo.

REFERENCES CITED

R. Bergan, et al (1996). Electroporation of synthetic oligonucleotides: a novel technique for ex vivo bone marrow purging. Blood 88: 731.
O. Boussif, et al. (1995). A versatile vector for gene and oligonucleotide transfer into cells in culture and in vivo: polyethyleneimine. Proceedings of the National Academy of Sciences, USA 92: 7297.

G. Chassaing, A Prochiantz (1997). Peptides usable as vectors for the intracellular addressing of active molecules. PCT published patent application WO 97/12912.

D. Chin, et al (1990). Rapid nuclear accumulation of injected oligodeoxyribonucleotides. New Biology 2: 1091.

P. Chou, G. Fasman (1974). Prediction of Protein Conformation. Biochemistry 13: 222.

D. Derossi, et al (1994). The third helix of the Antennapedia homeodomain translocates through biological membranes. The Journal of Biological Chemistry 269: 10444.

G. Elliott, P. O'Hare (1997). Intracellular trafficking and protein delivery by a herpesvirus structural protein. Cell 88: 223.

P. Feigner, G. Ringold (1987). Cationic liposome-mediated transfection. Nature 337: 387.

G. Hermanson (1996). Bioconjugate Techniques. Pub. By Academic Press, New York.

S. Kang, R. Cho, R. Kole (1998). Up-regulation of luciferase gene expression with antisense oligonucleotides: Implications and applications in functional assay development. Biochemistry 37: 6235

M. Lemaitre, B. Bayard, B. Lebleu (1987). Specific antiviral activity of a poly(L-lysine)-conjugated oligodeoxyribonucleotide sequence complementary to vesicular somatitis virus N protein mRNA initiation site. Proceedings of the National Academy of Sciences, USA 84: 648.

D. Mann, A. Frankel (1991). Endocytosis and targeting of exogenous HIV-1 tat protein. The EMBO Journal 10: 1733.

P. Morcos (2001). Achieving efficient delivery of Morpholino oligos in cultured cells. GENESIS: The Journal of Genetics and Development 30: 94.

P. Marcos, J. E. Summerton, J. P. Summerton (2001). Osmotic delivery composition, solution, and method. U.S. Pat. No. 6,228,392.

P. Midoux, et al (1998). Membrane permeabilization and efficient gene transfer by a peptide containing several histidines. Bioconjugate Chemistry 9: 260.

M. Murata, et al (1991). Membrane fusion induced by mutual interaction of the two charge-reversed amphiphilic peptides at neutral pH. Journal of Biological Chemistry 266: 14353

M. Murata, et al (1992). pH-dependent membrane fusion and vesiculation of phospholipid large unilamellar vesicles induced by amphiphilic anionic and cationic peptides. Biochem. 31: 1986.

M. Partridge, A. Vincent, P. Matthews, J. Summerton (1996). A simple method for delivering Morpholino antisense oligos into the cytoplasm of cells. Antisense & Nucleic Acid Drug Development 6: 169.

C. Pichon, et al (1997). Cytosolic and nuclear delivery of oligonucleotides mediated by an amphiphilic anionic peptide. Antisense and Nucleic Acid Drug Development 7: 335.

C. Pichon, et al (2000). Histidylated oligolysines increase the transmembrane passage and the biological activity of antisense oligonucleotides. Nucleic Acids Research 28: 504.

C. Plank, et al. (1994). The influence of endosome-disruptive peptides on gene transfer using synthetic virus-like gene transfer systems. Journal of Biological Chemistry 269:12918.

P. Sazani et al. (2002). Systematically delivered antisense oligomers upregulate gene expression in mouse tissues. Nature Biotechnology 20: 1228.

D. Spiller, D. Tidd (1995). Nuclear delivery of antisense oligodeoxynucleotides through reversible permeabilization of human leukemia cells with streptolysin 0. Antisense Research and Development 5: 13.

J. Summerton, D. Weller (1997). Morpholino antisense oligomers: design, preparation, and properties. Antisense & Nucleic Acid Drug Development 7: 187.

J. Summerton (1999). Morpholino antisense oligomers: the case for an RNase H-independent structural type. Biochemica et Biophysica Acta 1489: 141.

J. Summerton, D. Weller (2000). Polymer composition for delivering substances in living organisms. U.S. Pat. No. 6,030,941.

A. Thierry, A. Rahman, A. Dritschilo (1992). Liposomal delivery as a new approach to transport antisense oligonucleotides. In: R. Erickson & J. Izant; pages 147–157 of Gene Regulation: Biology of Antisense RNA and DNA. Raven Press, New York.

SCOPE OF THE INVENTION

The above presents a description of the best mode contemplated of carrying out the present invention, and of the manner and process of using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover all modifications and alternate constructions coming within the spirit and scope of the invention as generally expressed by the following claims, which particularly point out and distinctly claim the subject matter of the invention:

What is claimed is:

1. A peptide composition comprising
   (a) a peptide ranging in length from about 19 to about 37 amino acids,
   (b) said peptide having two faces when in an alpha helical conformation, consisting of a lipophilic face and a weak-base face,
   (c) the first face being a lipophilic face, wherein
      (i) 80% to 100% of the amino acids of the lipophilic face are selected from the group consisting of leucine, isoleucine, norleucine, valine and norvaline,
      (ii) none of the amino acids of the lipophilic face have side chains which carry an ionic charge at neutral pH,
      (iii) the lipophilic face size ranges from about 140 degrees to about 180 degrees, and
   (d) the second face being a weak-base face, wherein
      (i) 80% to 100% of the amino acids of the weak-base face are selected from the group consisting of histidine, lysine and arginine,
      (ii) at least 70% of the amino acids of the weak-base face are histidines,
      (iii) none of the amino acids of the weak-base face are acid amino acids,
      (iv) the weak-base face size ranges from about 180 degrees to about 220 degrees.

2. The peptide composition of claim 1 wherein the peptide ranges in length from 22 to 33 amino acids.

3. The peptide composition of claim 1 wherein the lipophilic face size is 160 degrees and the weak-base face size is 200 degrees.

4. The peptide composition of claim 1 wherein predominantly all of the amino acids of the lipophilic face are leucines.

5. The peptide composition of claim 1 wherein predominantly all of the amino acids of the weak-base face are histidines.

6. The peptide composition of claim 1 wherein up to 30% of the amino acids of the weak-base face are selected from the group of strong-base amino acids consisting of lysine and arginine.

7. The peptide composition of claim 6 wherein only one strong-base amino acid is present in any two consecutive alpha helical turns of the peptide.

8. The peptide composition of claim 1 wherein said peptide has a non-ionic C-terminus at neutral pH.

9. The peptide composition of claim 8 wherein the C-terminus includes an amide moiety.

10. The peptide composition of claim 1 which is linked to an antisense oligo.

11. The peptide composition of claim 10 wherein the antisense oligo is a Morpholino antisense oligo.

12. A method for delivering large polar substances into the cytosol of animal cells, said method comprising providing a peptide composition
    (a) ranging in length from about 19 to about 37 amino acids
    (b) having two faces when in an alpha helical conformation,
    (c) the first face being a lipophilic face, wherein
        (i) 80% to 100% of the amino acids of the lipophilic face are selected from the group consisting of leucine, isoleucine, norleucine, valine and norvaline, and
        (ii) none of the amino acids of the lipophilic face have side chains which carry an ionic charge at neutral pH, and
        (iii) the lipophilic face size ranges from about 140 degrees to about 180 degrees, and
    (d) the second face being a weak-base face, wherein
        (i) 80% to 100% of the amino acids of the weak-base face are selected from the group consisting of histidine, lysine, and arginine
        (ii) at least 70% of the amino acids of the weak-base face are histidines
        (iii) none of the amino acids of the weak-base face are acid amino acids,
        (iv) the weak-base face size ranges from about 180 degrees to about 220 degrees.
said method further comprising contacting both the peptide composition and the large polar substances with said animal cells.

13. The method of claim 12 wherein at least one of the large polar substances is a Morpholino antisense oligo.

14. The method of claim 12 wherein at least one of said peptide composition is linked via a disulfide bond to at least one of the large polar substances.

15. The method of claim 14 wherein at least one of the large polar substances is a Morpholino antisense oligo.

16. The method of claim 12 wherein the peptide composition is first dissolved in a solvent selected from the group consisting of
    a. 20% water and 80% ethanol;
    b. 150 milliMolar aqueous sodium chloride plus 1 equivalent of acetic acid per equivalent of side chain base in the delivery peptide;
    c. 300 milliMolar aqueous sorbitol, plus 1 equivalent of acetic acid per equivalent of side chain base in delivery peptide;
    d. dimethylsulfoxide.

17. The method of claim 12 wherein the peptide composition is first dissolved in an aqueous solution of dimethylsulfoxide, wherein the dimethylsulfoxide concentration ranges from about 15% to about 60% by volume.

18. The method of claim 12 wherein the peptide composition is first suspended in an aqueous solution which is low in salt and near isotonic, and wherein before use the solution is heated to about 50 deg. C. or above and then slow cooled to give a homogeneous solution.

19. The method of claim 16 wherein the peptide composition is dissolved in dimethylsulfoxide at a concentration ranging from about 1 milliMolar to about 3 milliMolar.

20. The method of claim 12 wherein the concentration of the peptide composition contacted with the animal cells is in the range of about 6 microMolar to about 20 microMolar.

21. The method of claim 12 wherein at least one of the large polar substances is selected from the group consisting of antisense oligos, ribozymes, interfering RNA, small interfering RNA, peptides, proteins, oligonucleotides, polynucleotides, and pharmaceuticals which achieve their effect in the cytosol/nuclear compartment of animal cells.

22. A method for treating a live animal by delivering large polar substances into the cytosol of cells in that animal, said method comprising providing a peptide composition
    (a) ranging in length from about 19 to about 37 amino acids;
    (b) having two faces when in an alpha helical conformation;
    (c) the first face being a lipophilic face, wherein
        (i) 80% to 100% of the amino acids of the lipophilic face are selected from the group consisting of leucine, isoleucine, norleucine, valine and norvaline;
        (ii) none of the amino acids of the lipophilic face have side chains which carry an ionic charge at neutral pH; and
        (iii) the lipophilic face size ranges from about 140 degrees to about 180 degrees; and
    (d) the second face being a weak-base face, wherein
        (i) 80% to 100% of the amino acids of the weak-base face are selected from the group consisting of histidine, lysine, and arginine
        (ii) at least 70% of the amino acids of the weak-base face are histidines
        (iii) none of the amino acids of the weak-base face are acid amino acids,
        (iv) the weak-base face size ranges from about 180 degrees to about 220 degrees;
said method further comprising introducing both the peptide composition and the large polar substances into said animal.

23. The method of claim 22 wherein at least one of said peptide composition is linked to at least one of the large polar substances.

24. The method of claim 22 wherein at least one of the large polar substances is a therapeutic agent which acts within the cytosol/nuclear compartment of the cells of said animal.

25. The method of claim 24 wherein at least one of said therapeutic agents is a Morpholino antisense oligo.

26. The method of claim 22 wherein the live animal is a human.

* * * * *